United States Patent [19]

Uchikubo et al.

[11] Patent Number: 5,678,568
[45] Date of Patent: Oct. 21, 1997

[54] SYSTEM CONTROL APPARATUS, MEDICAL SYSTEM CONTROL APPARATUS AND IMAGE-PLANE DISPLAY METHOD OF MEDICAL SYSTEM CONTROL APPARATUS

[75] Inventors: Akinobu Uchikubo, Oume; Akihiro Taguchi, Hachioji; Junichi Onishi, Hachioji; Kyou Imagawa, Hachioji; Yasukazu Tatsumi, Hino; Yukiko Nagaoka, Fuchu; Yoshito Ichikawa, Saitama-ken; Mamoru Kaneko, Hannou; Tsutomu Hirai, Hachioji; Kuniaki Kami, Machida; Satoshi Takemoto, Oume; Kouji Tanikawa, Hachioji; Kenji Harano, Hachioji; Hiroshi Takahashi, Hachioji; Makoto Tsunakawa, Choufu; Kenya Inomata, Mitaka, all of Japan

[73] Assignee: Olympus Optical Co., Ltd., Tokyo, Japan

[21] Appl. No.: 278,940

[22] Filed: Jul. 22, 1994

[30] Foreign Application Priority Data

Jul. 27, 1993 [JP] Japan .................... 5-184869
Nov. 9, 1993 [JP] Japan .................... 5-279821
Nov. 9, 1993 [JP] Japan .................... 5-279822
Dec. 27, 1993 [JP] Japan .................... 5-330140

[51] Int. Cl.[6] .................................... A61B 19/00
[52] U.S. Cl. ................................................ 128/897
[58] Field of Search ................... 364/413.01–413.03; 128/897–898

[56] References Cited

U.S. PATENT DOCUMENTS 4,756,706 7/1988 Kerns et al. .................. 364/413.01
5,249,121 9/1993 Baum et al. .
5,331,549 7/1994 Crawford, Jr. ................ 364/413.02

FOREIGN PATENT DOCUMENTS 5-153670 6/1993 Japan .

Primary Examiner—Angela D. Sykes
Assistant Examiner—John P. Lacyk
Attorney, Agent, or Firm—Armstrong, Westerman, Hattori, McLeland & Naughton

[57] ABSTRACT

A medical system control apparatus including a plurality of pieces of medical equipment having respective identification numbers thereof individually, and having display portions on which setting conditions or operating conditions are displayed and operating portions for modifying the setting conditions or the operating conditions which are displayed on the display portions, a centralized controller for controlling the plurality of pieces of medical equipment, a centralized display device connected to the controller and provided with a display portion which displays the display contents of the plurality of pieces of medical equipment, a centralized operation device connected to the controller for controlling the setting conditions or the operating conditions which are displayed on the display portions of the plurality of pieces of medical equipment, and a communication device for enabling the plurality of pieces of medical equipment, the centralized display device and the centralized operation device and the controller to communicate with each other in a bidirectional manner.

28 Claims, 28 Drawing Sheets

FIG.26
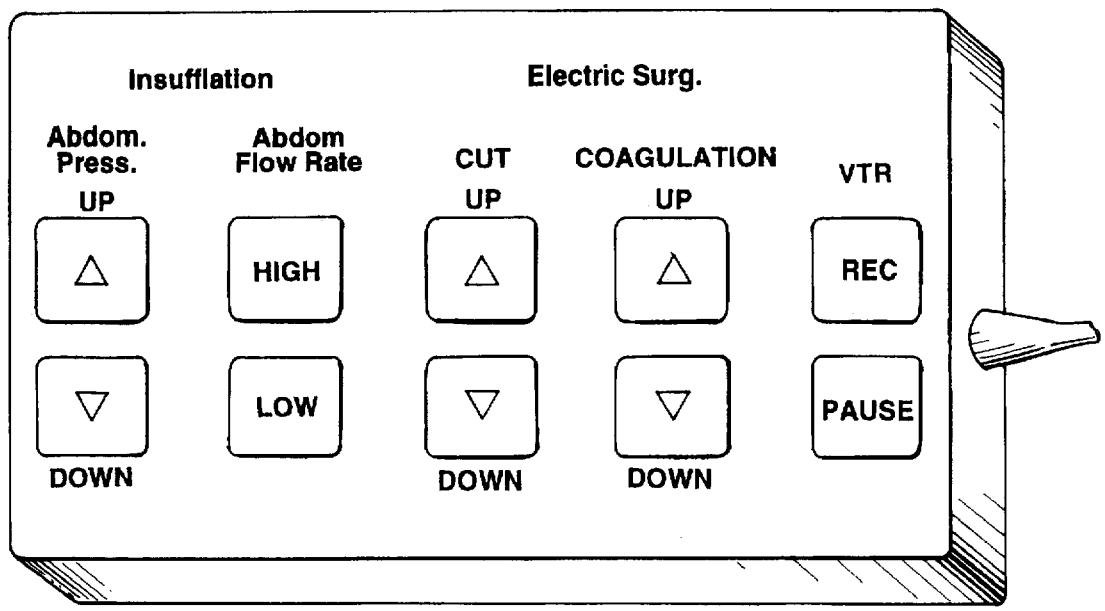
FIG.27A
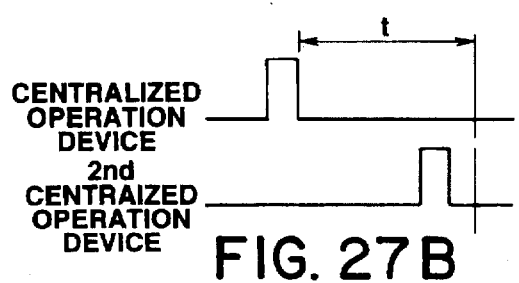
FIG. 27B
FIG.28A
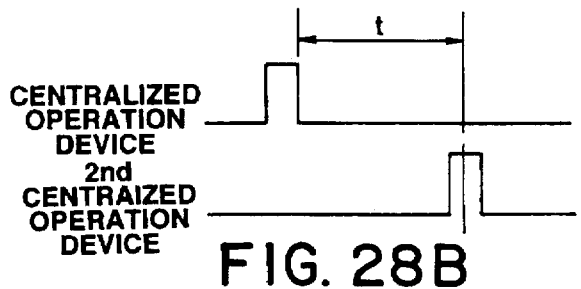
FIG. 28B
FIG.29A
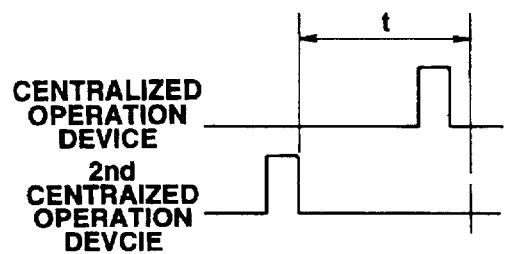
FIG. 29B
FIG.30A
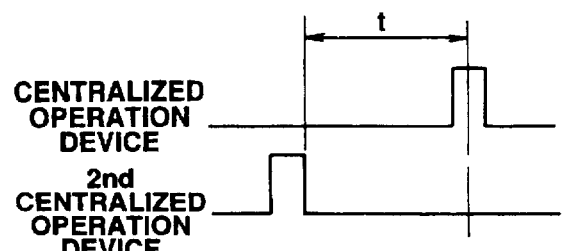
FIG. 30B

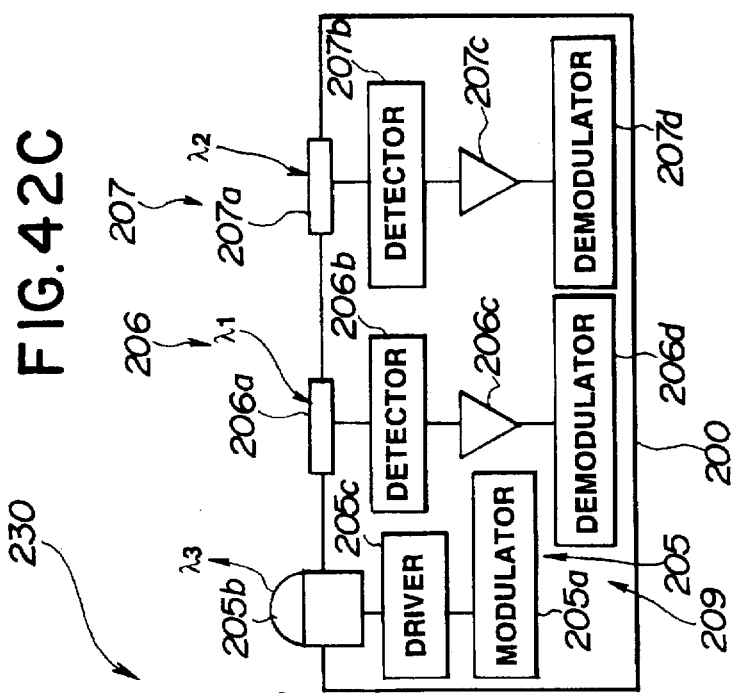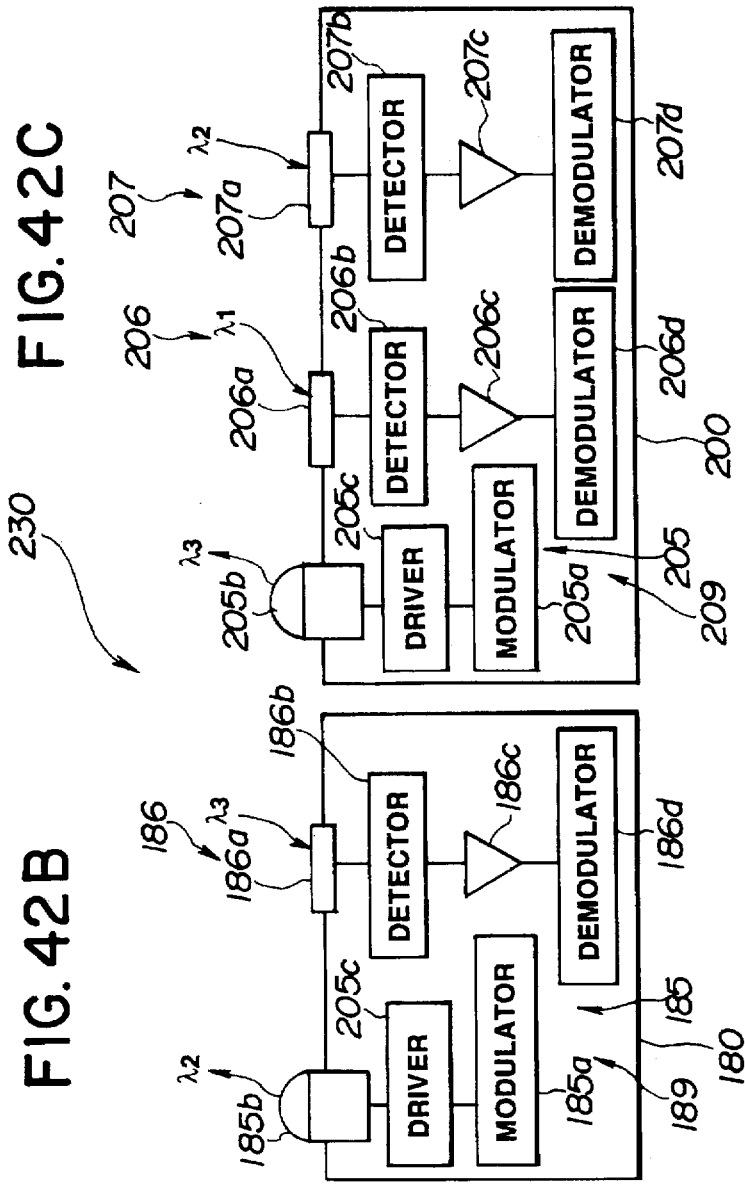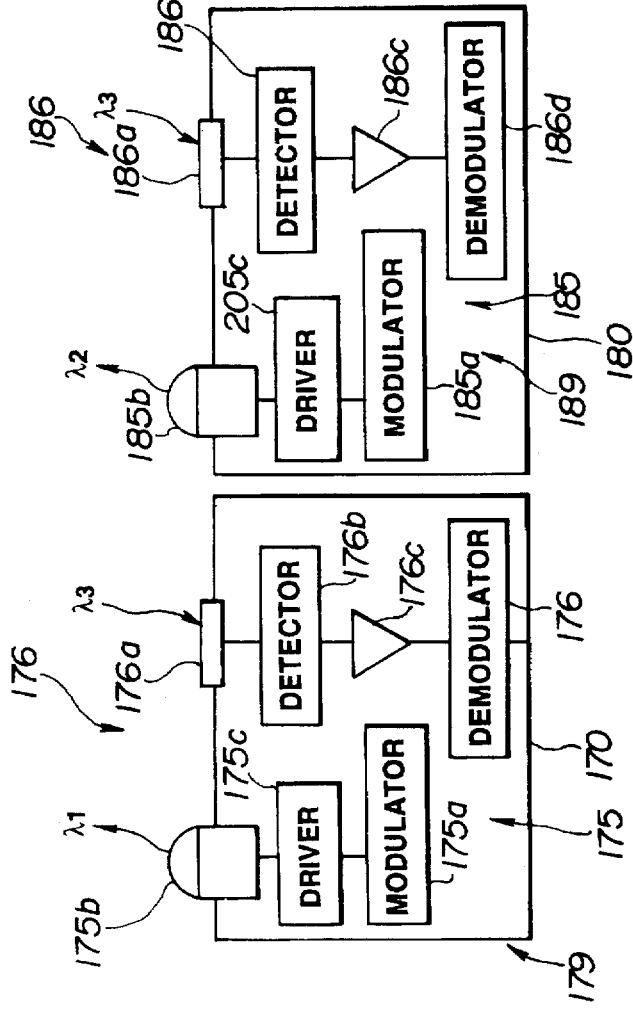

SYSTEM CONTROL APPARATUS, MEDICAL SYSTEM CONTROL APPARATUS AND IMAGE-PLANE DISPLAY METHOD OF MEDICAL SYSTEM CONTROL APPARATUS

BACKGROUND OF THE INVENTION

1. Field of the Invention

The present invention relates to a system control apparatus for controlling, in a centralized manner, a plurality of pieces of equipment to be controlled and, more particularly, to a medical system control apparatus which discriminates or identifies a plurality of pieces of medical equipment individually to control, in a centralized manner, setting conditions or operating conditions of respective pieces of pieces of medical equipment.

2. Description of Related Art

Generally, operation is performed in such a manner that a plurality of pieces of pieces of medical equipment in accordance with operation objects are prepared, and the operation is performed by the use of these pieces of medical equipment. Operating doctors and pieces of medical equipment which are used by the operating doctors are arranged in a sterile area within the operating chamber, and various pieces of medical equipment which are provided with display portions for setting conditions and operating conditions which are displayed on the display portions, and operating portions are arranged in a unsterile area. For this reason, operation of the various pieces of medical equipment which are arranged in the unsterile area is performed by full-time operators or nurses who are in the unsterile area, and who receive instructions from the operating doctors in the sterile area. Accordingly, there is no situation where the operating doctors directly operate the various pieces of medical equipment which are arranged in the unsterile area. However, functions of these respective pieces of medical equipment are individually independent from each other, and there are many cases where the functions of the respective pieces of medical equipment are inadequate for composite using modes. Upon operation, since an operator moves between the various pieces of medical equipment in accordance with the instructions from the operating doctors to operate the various pieces of medical equipment, high degree of skill from the operator has been required in an operation which occurs in real time.

Moreover, there exist various pieces of medical equipment which are provided with communication ports. However, the communication ports are for displaying and outputting data, such as a printer, a monitor or the like. The arrangement is not an arrangement in which the pieces of medical equipment, or the pieces of medical equipment and computers are connected to each other for communication, and the arrangement is systematically formed.

For this reason, the operators or nurses are assigned or allocated every piece of medical equipment, or a plurality of pieces of medical equipment are in the charge of a small number of operators, and the plurality of pieces of medical equipment are operated in accordance with the instructions of the operating doctors, in order to enable that these pieces of medical equipment are used in an operating chamber compositely and in real time.

As a result, there are the following disadvantages. That is, all the pieces of medical equipment in accordance with operations are set and prepared in the operating chamber. The interior of the operating chamber is overrun by the pieces of medical equipment; the operability or workability is deteriorated, and a bad influence is exerted also upon the proceeding of the operation.

SUMMARY OF THE INVENTION

It is an object of the invention to provide a system control apparatus which facilitates systematization of a plurality of devices to be controlled, and which enables operation of independent devices to be performed, which enables compound or composite gang or interlocking operation connected between the devices to be performed, and which enables centralized control of the plurality of devices to be controlled to be performed so that operability is superior.

Another object of the invention is to provide a medical system control apparatus which facilitates systematization of a plurality of pieces of medical equipment and which enables independent operation of the pieces of medical equipment, which enables composite gang or interlocking operation connected between the pieces of medical equipment, and which enables centralized management and centralized control of respective operating conditions or respective setting conditions of the plurality of pieces of medical equipment, so that operability is superior.

Another object of the invention is to provide an image-plane display method of a medical system control apparatus in which at least one of setting conditions and operating conditions which are displayed respectively on a plurality of pieces of medical equipment or error information or the like is displayed on a display monitor such that a user easily understands the at least one condition and the error information.

According to the present invention, there is provided a system control apparatus comprising a plurality of devices to be controlled having identification numbers individually, control means for controlling, in a centralized manner, these plurality of devices to be controlled, and communication means for enabling the devices to be controlled and the control means to be communicated, in a bidirectional manner, to each other.

According to the present invention, there is further provided a medical system control apparatus which comprises a plurality of pieces of medical equipment having respective discrimination or identification numbers thereof individually and having display portions on which respective setting conditions or respective operating conditions are displayed, and operating portions for changing or modifying the setting conditions or the operating conditions which are displayed on the display portion; control means for controlling, in a centralized manner, the plurality of pieces of medical equipment; and communication means for enabling the plurality of medical equipment and the control means to be communicated, in a bidirectional manner, to each other, wherein at least one of centralized display means provided with a display portion for displaying the display contents of the plurality of pieces of medical equipment, and centralized operation means having a display portion for displaying the display contents of the plurality of pieces of medical equipment for controlling the setting conditions or the operating conditions of these pieces of medical equipment is connected to the control means, and wherein an image plane which displays the contents of a specific function of the plurality of pieces of medical equipment is provided on at least one of the centralized display means and the display portion of the centralized operation means.

Also according to the present invention, there is provided an image-plane display method of pieces of a medical system control apparatus comprising a control method for controlling, in a centralized manner, a plurality of pieces of medical equipment having display portions on which setting conditions or operating conditions are displayed and operating portions for changing or modifying the setting conditions or the operating conditions displayed on a display portion, through control means, having identification numbers individually; a centralized display method for displaying the display contents of the plurality of pieces of medical equipment which are controlled by the control method, on the display portion of the centralized display means to display the contents of specific functions of the plurality of pieces of medical equipment; a centralized operation method having a display portion for displaying the display contents of the plurality of pieces of medical equipment which are controlled by the control method to control the setting conditions or the operating conditions which are displayed on the display portions of these pieces of medical equipment; and a communication method for enabling the plurality of pieces of medical equipment, the centralized display means, and the centralized operation means and the control means to be in communication, in bidirectional manner, with each other, wherein a desired image plane is selected and displayed from hierarchy image planes in which an image plane for displaying the contents of specific functions of the plurality of pieces of medical equipment, an image plane for displaying the contents of the setting conditions or the operating conditions which are displayed on the display portions which are had respectively by the plurality of pieces of medical equipment and a backup image plane for storing or retaining a predetermined operating condition of the piece of medical equipment which is extracted among the plurality of pieces of medical equipment are hierarchically arranged, on at least one of centralized display means provided with a display portion for displaying the setting conditions or the operating conditions of the plurality of pieces of medical equipment and a display portion of the centralized operating means for controlling the setting conditions or the operating conditions of these pieces of medical equipment.

These objects and advantages of the present invention will become further apparent from the following detailed explanation.

BRIEF DESCRIPTION OF THE DRAWINGS

FIG. 2 is a view showing an arrangement of a control system of a device to be controlled;

FIG. 3 is a conceptional view of a format where information is transmitted in the form of a packet;

FIG. 5 is an explanatory view showing an arrangement of an observation device which includes an endoscope in the medical endoscope system;

FIG. 6 is an explanatory view showing a console panel of an endoscope camera device;

FIG. 7 is an explanatory view showing a console panel of an endoscope light source device;

FIG. 8 is an explanatory view showing a console panel of an electrical surgical instrument;

FIG. 9 is an explanatory view showing a console panel of an insufflation device;

FIG. 10 is an explanatory view showing a device arrangement and an in-use condition where the medical endoscope system is used to perform an endoscope operation;

FIG. 11 is an explanatory view showing an arrangement example of a plurality of pieces of medical equipment which form the medical endoscope system;

FIG. 13 is an explanatory view showing a display image-plane arrangement of a centralized display panel of a centralized operation device;

FIG. 14 is a view showing a condition in which a console panel of an electrical surgical instrument is indicated on the centralized display panel to a centralized operation device;

FIG. 15 is an explanatory view showing an example of abnormal display at the time the system is abnormal;

FIG. 16 is an explanatory view showing another example of abnormal display at the time the system is abnormal;

FIG. 17 is an explanatory view showing the other example of abnormal display at the time the system is abnormal;

FIG. 18 is an explanatory view showing still another example of abnormal display at the time the system is abnormal;

FIG. 19 is an explanatory view showing an example of an image plane which notifies connection failure of the pieces of medical equipment;

FIG. 20 is an explanatory view showing another example of the image plane which notifies connection failure of the pieces of medical equipment;

FIG. 21 is an explanatory view showing the other example of the image plane which notifies connection failure of the pieces of medical equipment;

FIG. 22 is an explanatory view showing still image plane which notifies another example of the connection failure of the pieces of medical equipment;

FIGS. 24 to 30 show a fourth embodiment of the invention, FIG. 24 being a block diagram showing the entire or whole arrangement of a medical endoscope system;

FIG. 25 is an explanatory view showing the positional relationship between pieces of medical equipment and an operating doctor and an operator within an operation chamber;

FIG. 26 is an explanatory view showing an arrangement of a second centralized operation device;

FIG. 27 is a timing chart showing a condition under which an indicating signal is inputted from a second centralized operation device successively to a centralized operation device within a predetermined period time;

FIG. 28 is a timing chart showing a condition under which the indicating signal is inputted from the second centralized operation device successively to the centralized operation device after a predetermined period of time;

FIG. 29 is a timing chart showing a condition under which the indicating signal is inputted from the centralized operation device successively to the second centralized operation device within a predetermined period of time;

FIG. 30 is a timing chart showing a condition under which the indicating signal is inputted from the centralized operation device successively to the second centralized operation device after a predetermined period of time;

FIG. 32 is a view showing the relationship between the angle adjustment means and a field-of-view;

FIG. 33 is a view showing another example of the display panel which is provided with the angle adjustment means on a planar portion which is coplanar to an image display portion;

FIG. 34 is a view showing the other example of the display panel which is provided with the angle adjustment means on the planar portion which is coplanar to the image display portion;

FIGS. 35 to 42 show a sixth embodiment of the invention, FIG. 35 being an explanatory view of a centralized display panel of an endoscope operation unit disposed or arranged at another position;

FIG. 36 is an explanatory view showing the disposition or arrangement positional relationship of a connector group, a CO2 bomb and a suction bottle of the endoscope operation unit;

FIG. 37 is a view showing the connector group of the endoscope operation unit; and FIGS. 38 to 42 relate to the sixth embodiment of the invention. FIG. 38 being a view showing a schematic arrangement of the medical system control apparatus which is provided with an optical communication device;

FIG. 39 being an explanatory view showing a schematic arrangement of the optical communication device;

FIG. 40 being a view showing another arrangement of the medical system control apparatus which is provided with the optical communication device;

FIG. 41 being a view showing the other arrangement of the medical system control apparatus which is provided with the optical communication device; and FIG. 42 being a view showing still another arrangement of the medical system control apparatus which is provided with the optical communication device.

DETAILED DESCRIPTION OF THE PREFERRED EMBODIMENTS

A first embodiment of the invention will be described with reference to FIGS. 1 to 3.

Figure 1:
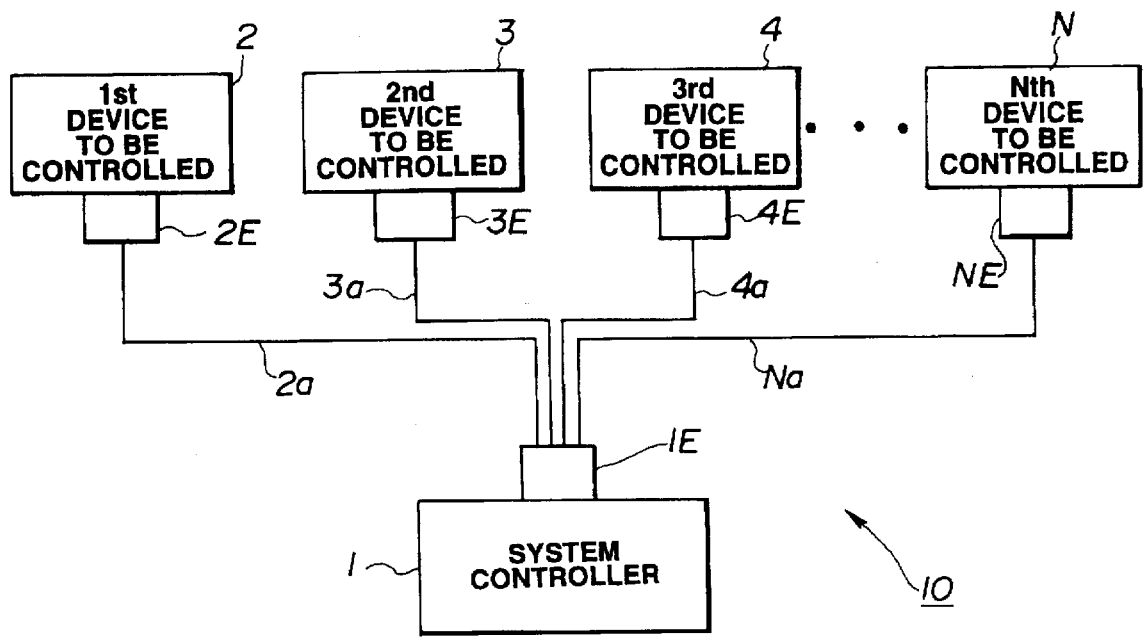
FIGS. 1 to 3 show a first embodiment of the invention, FIG. 1 being an arrangement diagram of a system control apparatus.

As shown in FIG. 1, a system control apparatus 10 according to the present embodiment of the invention is arranged such that a plurality of pieces of equipment to be controlled 2, 3, ... N to which identification (ID) numbers are assigned or allocated respectively without being overlapped to each other individually, and a system controller 1 that is an example of control means are connected to each other so as to be capable of being communicated to each other, in a bidirectional manner, through, for example, communication cables 2a, 3a, ... Na that are communication means.

Figure 2:
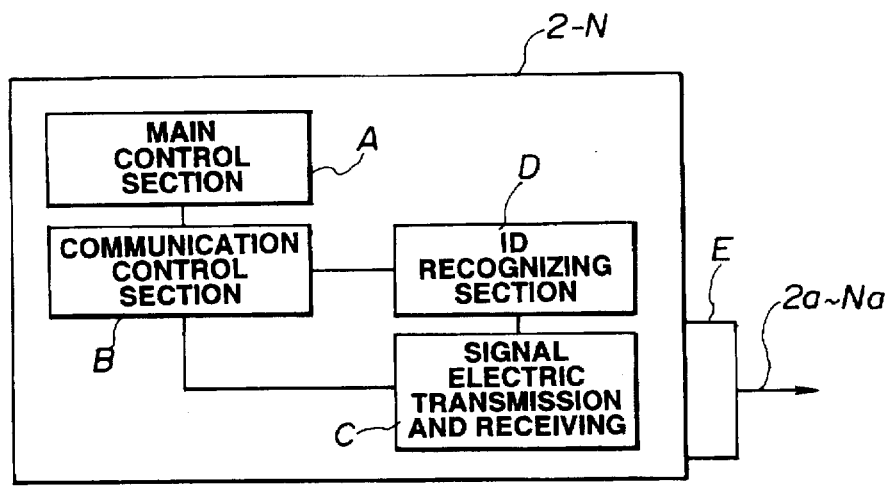

As shown in FIG. 2, a main control section A which performs setting-condition control peculiar to the pieces of equipment to be controlled, a communication control section B which performs control of communication, a signal transmission and receiving section C for transmitting and receiving signals such as data or the like and an ID identifying section D which identifies IDs are provided within the plurality of pieces of equipment to be controlled 2, 3, ~N. Further, a communication port E which connects the communication cables 2a, 3a, ... Na for performing bidirectional communication with each other is provided on the outside of the pieces of equipment to be controlled 2, 3, ~N.

ID numbers assigned to or allocated to the respective equipments to be controlled, command data, addresses, codes for correcting and detecting errors of the communication signal or the like are communicated to and received from each other between the plurality of pieces of equipment to be controlled 2, 3, ... N and the system controller 1 as a single command packet.

Figure 3:
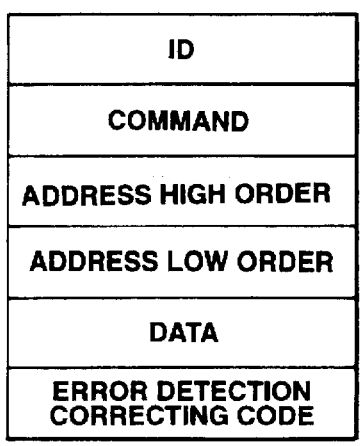

Specifically, as shown in FIG. 3, in case where the ID codes, the commands, the addresses, the data and the error detection correcting codes are transmitted as the single command packet, a device to be controlled which is operated by the ID codes is first specified, and a device to be controlled which is specified by a subsequent command is turned ON. Subsequently, a region which stores data for controlling the operating condition of the devices to be controlled which are turned ON at a high order address and at a low order address is secured and, then, the data are transmitted.

The data are a condition that is a first command, the data contents which perform operation for a period of time, data which include therein the contents in which, thereafter, the first command stops, data which include the contents which operate still another device to be controlled or like.

Moreover, error detection correcting codes are added thereto and are sent such that the commands or the like are detected without an error. Even if error detection correcting codes are transmitted in order of the ID codes, the commands, ...as shown in the figures, the error detection correcting codes may be transmitted as a packet with which the error detection correcting codes are mixed.

In connection with the above, it is judged whether or not it is coincident with the transmitted ID codes in the respective devices to be controlled. The pieces of medical equipment having coincident ID codes perform operation corresponding to the commands or the like which are subsequent after the ID codes.

In this manner, the identification numbers are individually provided on the plurality of devices to be controlled, and these devices to be controlled are connected to the system controller so as to be capable of being transmitted in a bidirectional manner, whereby the plurality of devices to be controlled can be controlled, in a centralized manner, by the system controller.

A second embodiment of the invention will be described with reference to FIGS. 4 to 11.

The present embodiment will now be described as a medical endoscope system which is one of medical system control apparatuses which control, in a centralized manner, a plurality of pieces of medical equipment.

Figure 4:
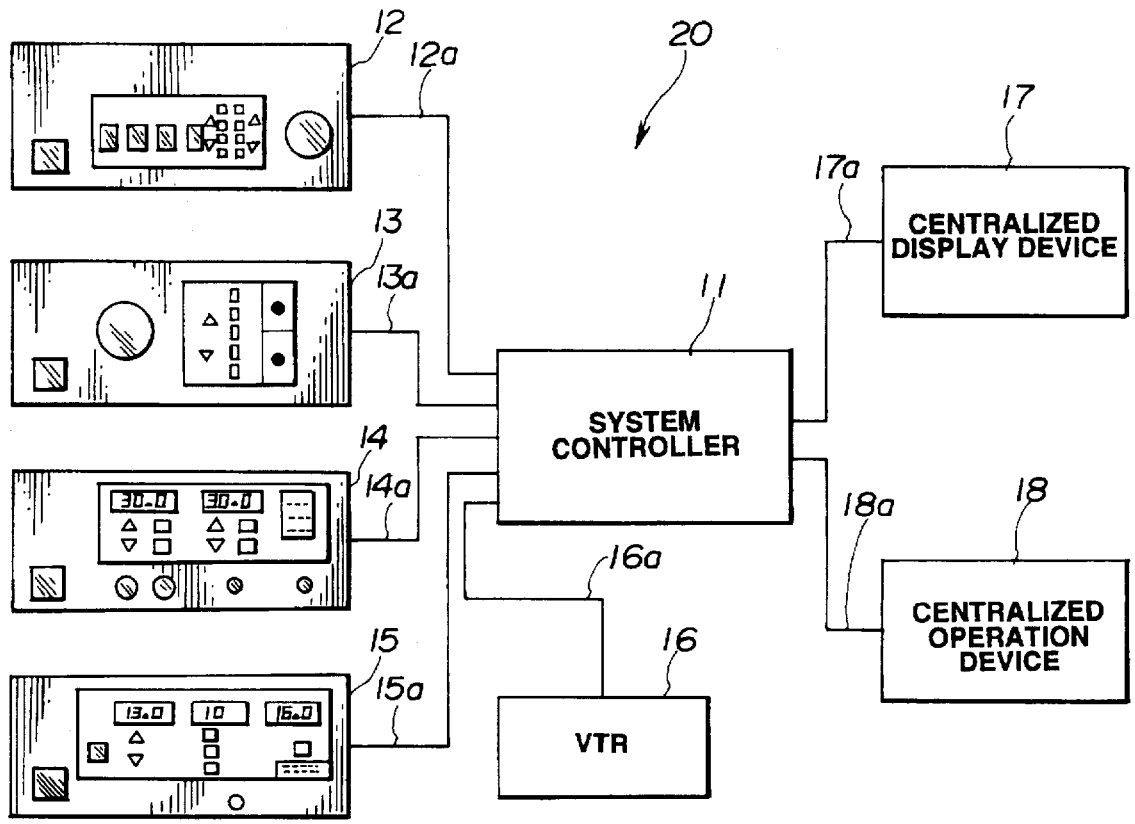
FIGS. 4 to 11 show a second embodiment of the invention, FIG. 4 being a block diagram showing the entire or whole arrangement of a medical endoscope system.

As shown in FIG. 4, a medical endoscope system 20 is arranged such that peculiar ID numbers which are different in function from each other and which come into objects to be controlled by a system controller 11 which performs centralized control are allocated or assigned to the system controller 11. An endoscope camera device 12 to which an endoscope to be described later, for example is connected, an endoscope light source device 13, an electrical surgical instrument 14, an insufflation device 15, a VTR 16 and the like are connected to each other, as pieces of medical equipment having respective display portions thereof on which setting conditions or operating conditions are displayed and respective operating portions thereof which modify the setting conditions or the operating conditions displayed on the display portion, so as to be capable of performing bidirectional communication, through communication cables 12a, 13a, 14a, 15a, and 16a. A centralized operation device 18 serving as centralized operation means which controls, in a centralized manner, the setting conditions or the operating conditions of the pieces of medical equipment and a centralized display device 17 serving as centralized display means provided with a display portion which displays the display contents which are displayed on the display portions of the plurality of pieces of medical equipment are connected through communication cables 17a and 18a, respectively, so as to be capable of performing bidirectional communication.

Figure 5:
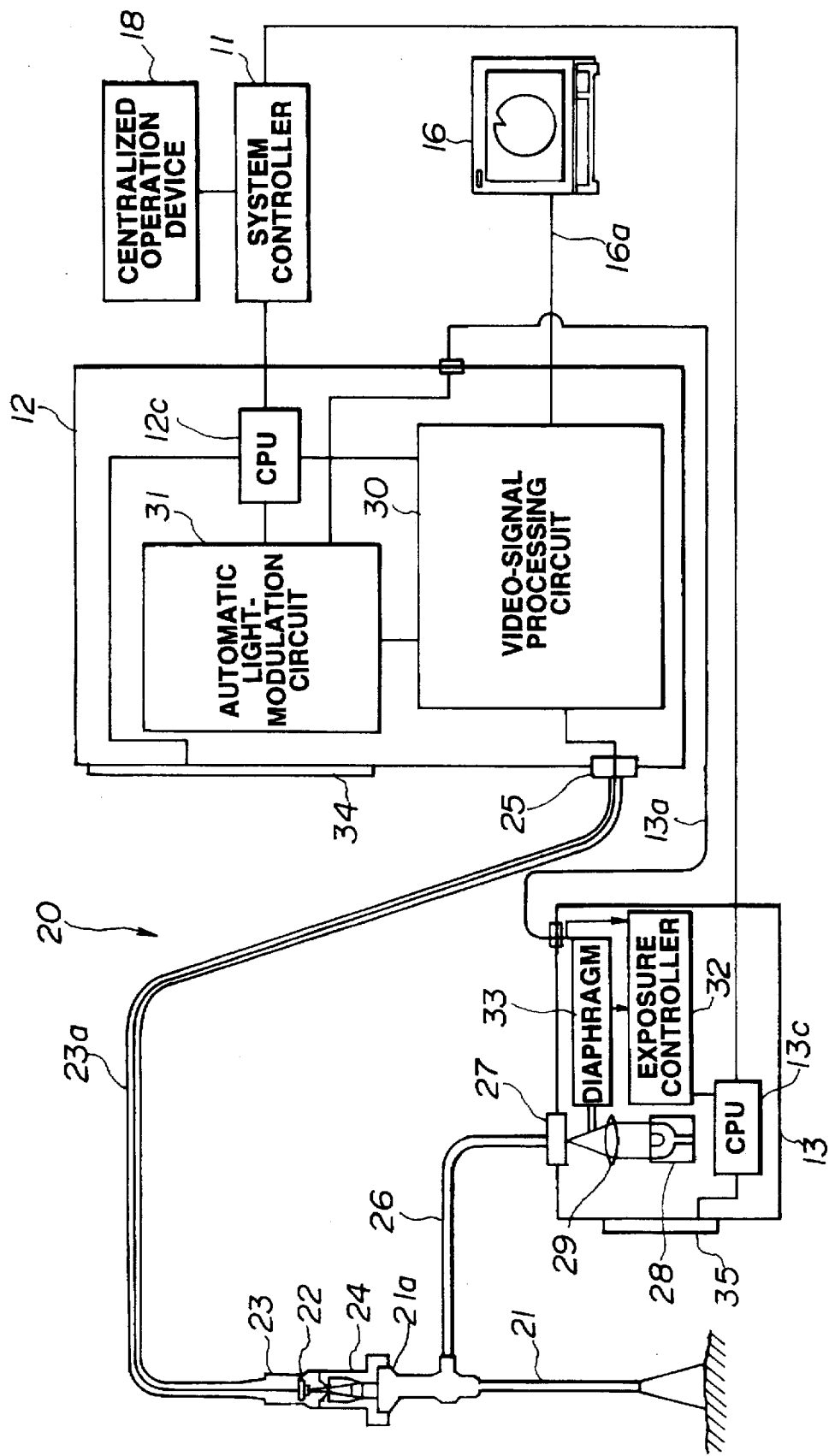

As shown in FIG. 5, a camera head 23 provided with a solid-state image pickup element 22 which photoelectrically converts a subject image which is taken by an endoscope 21, at a forward end thereof, for example, is detachable to an ocular portion 21a of the endoscope 21 which comes into a principal portion which forms the medical endoscope system 20, through a camera adaptor 24. An electrical signal of the subject image which is produced by the camera head 23 is transmitted to the endoscope camera device 12 through a connection cable 23a so as to be produced into a video signal. In this connection, the connection cable 23a is mounted, in an insertable manner, on and demounted from the endoscope camera device 12 by a connector 25 which is provided on a proximal portion of the connection cable 23a.

A light guide 26 extends from the side of a rearward end of the endoscope 21. The light guide 26 is detachably connected to a light guide connector 27 of the light source device 13 which supplies an illumination light.

The illumination light which is generated by a lamp 28 which is provided at the light source device 13 passes through a condensing lens 29, and is condensed to an end face of the light guide 26. The illumination light passes through the light guide 26 and is emanated from the forward end portion of the endoscope 21 to illuminate the interior of the body cavity. The illumination light is reflected with respect to a subject, and an image of the subject is formed in the endoscope 21. The subject image is picked up by the solid-state image pick-up element 22 of the camera head 23, and is converted into an electrical signal so as to be transmitted to the endoscope camera device 12.

A video-signal processing circuit 30 for converting the electrical signal that is an output from the solid-state image pickup element 22 to a video signal, and an automatic light modulation circuit 31 for producing a light control signal for adjusting a quantity of illuminating light of the light source device 13 on the basis of an output signal level of the solid-state image pickup element 22 are provided so as to be connected to a CPU 12c which governs control, on the endoscope camera device 12. The video signal which is converted by the video-signal processing circuit 30 is sent to the monitor 16 to display a subject image, while a light control signal which is produced by the automatic light modulation circuit 31 is transmitted to a CPU 13c of the light source device 13 through the CPU 12c and the system controller 11. The light control signal is sent from the CPU 13c to an exposure controller 32 to control, in opening and closure, a stop 33, to thereby adjust the quantity of illumination light which is outputted from the light source device 13, to an adequate value.

In connection with the above, since console panels 34 and 35 having respective display portions thereof for displaying operating conditions of respective apparatuses and respective operating portions thereof for changing or modifying the operating conditions are so provided as to be connected to the system controller 11 through the CPUs 12c and 13c, on front surfaces of the endoscope camera device 12 and the light source device 13, operation of the console panels 34 and 35, not only the centralized operation device 18, enables the operating conditions of the video-signal processing circuit 30 and the automatic light modulation circuit 31 of the endoscope camera device 12 and the exposure controller 32 of the light source device 13 to be controlled.

Here, the console panel 34 of the endoscope camera device 12, a console panel 35 of the endoscope light source device 13, a console panel 36 of the electrical surgical instrument 14 and a console panel 37 of the insufflation device 15 will be described with reference to FIGS. 6 to 9.

Figure 6:
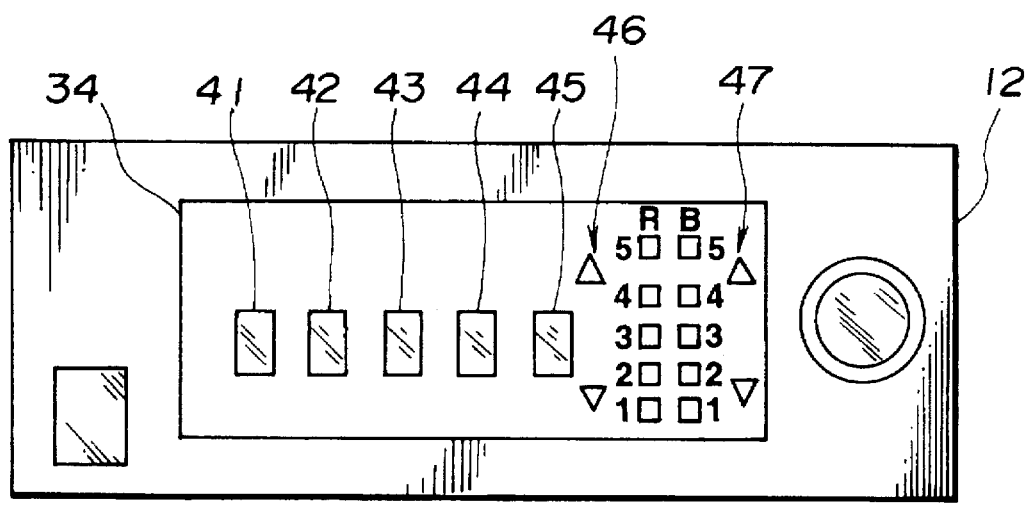

As shown in FIG. 6, various operating switches including a white balance 41, a photometry mode 42, an AGC 43, an outline emphasis 44, a color bar 45, a red tone regulation or adjustment 46 and a blue tone adjustment 47 are provided on the console panel 34.

Figure 7:
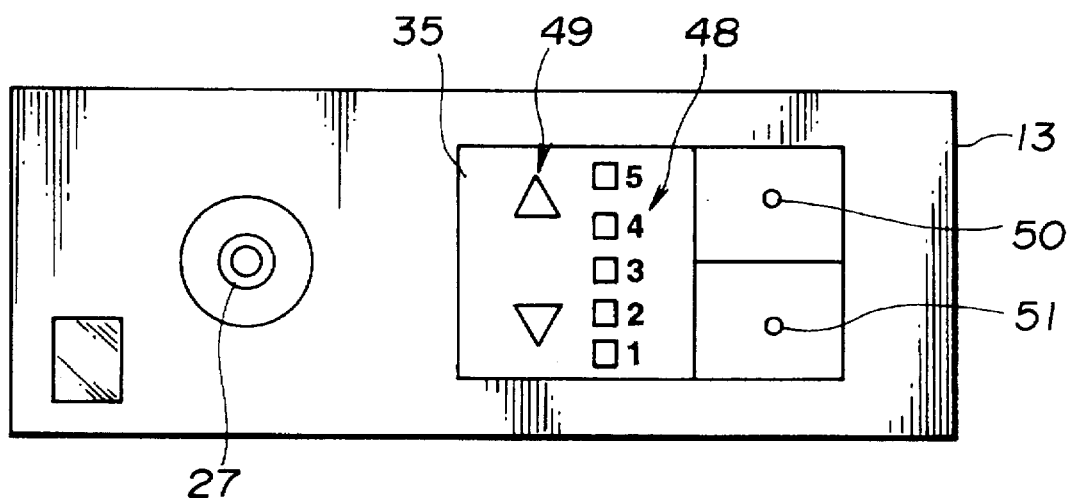

As shown in FIG. 7, a display portion 48 for displaying a brightness condition, a switch of a light quantity adjustment 49, an identifying LED 50 of an illumination mode of a lamp and a lamp running-out warning LED 51 are provided on the console panel 35 of the endoscope light source device 13.

Figure 8:
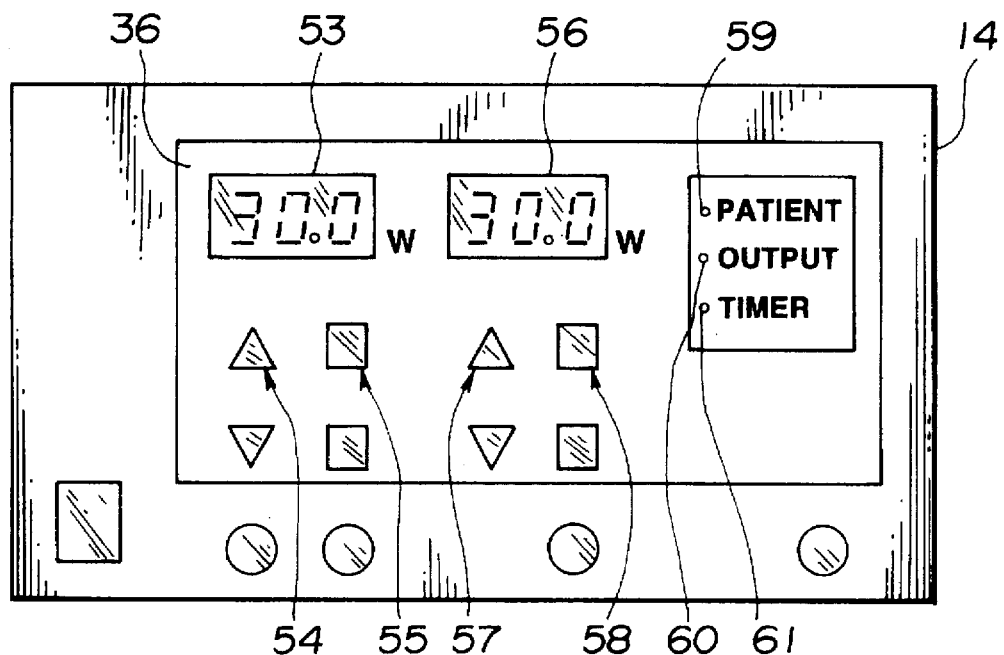

As shown in FIG. 8, a switch of an output level setting 54 in a CUT mode and output waveform switching 55 for removing or excising a tissue, a 7-segment displayer 53 for displaying a setting output of the CUT mode, a switch of output level setting 57 and output waveform switching 58 in a COAGULATION mode for coagulating the tissue, a 7-segment displayer 56 for displaying the setting output in the COAGULATION mode, an abnormal warning LED 59 of a P-plate of the apparatus, an output level abnormal warning LED 60 of the apparatus and an abnormal continuous output warning LED 61 of the apparatus are provided on the console panel 36 of the electrical surgical instrument 14.

Figure 9:
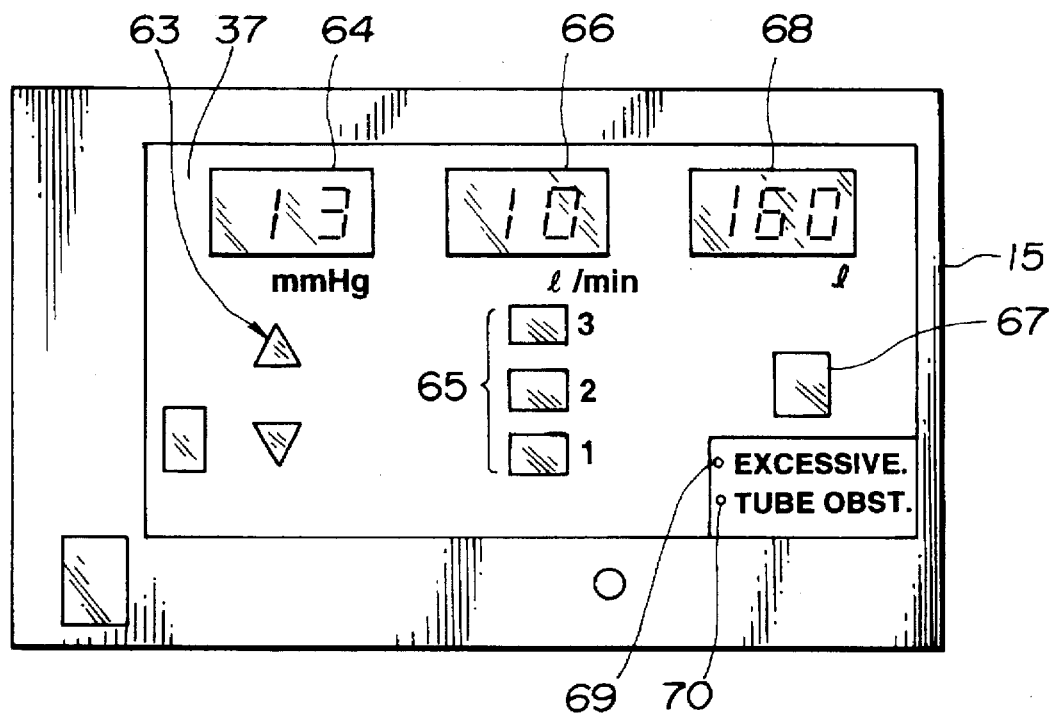

As shown in FIG. 9, a switch of abdomen pressure setting 63 and a 7-segment displayer 64 for displaying abdomen pressure, a switch for carbon dioxide gas flow-rate setting 65 and a 7-segment displayer 66 for displaying carbon dioxide gas flow-rate, a counter resetting switch 67 of consumption of the carbon dioxide gas, a 7-segment displayer 68 for displaying consumption of the carbon dioxide gas, an over-meteorismus pneumatics warning LED 69, a meteorismus pneumatics tube clogging warning LED 70 are provided on the console panel 37 of the insufflation device 15.

In this manner, since, in the medical endoscope system, at least one of the setting conditions and the operating conditions of various pieces of medical equipment can be controlled by both the centralized operating device and the console panels provided respectively on the various pieces of medical equipment, even in case where a system is formed by a plurality of pieces of medical equipment, operation at the console panels which are provided respectively on the pieces of medical equipment is made possible.

Figure 10:
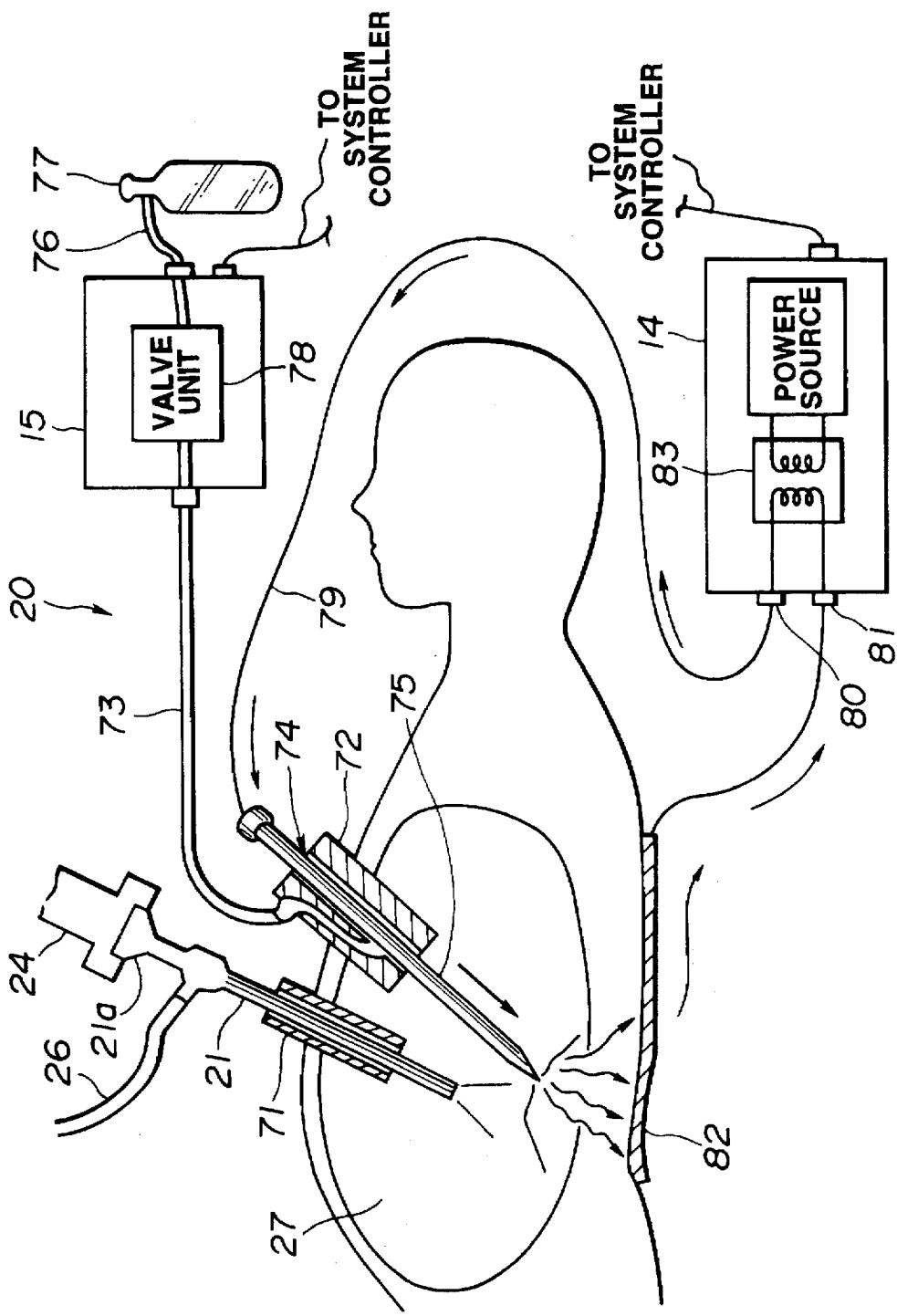

In connection with the above, the control priority order between the various pieces of medical equipment and the centralized operating device is made to the following relationship:

Console panels of the respective pieces of medical equipment>Concentrated operating device FIG. 10 shows a condition under which the endoscope camera device 12 of the medical endoscope system 20, the endoscope light source device 13, the electrical surgical instrument 14 and the insufflation device 15 are used to perform endoscopic operation. Guide tubes (hereinafter referred to as "trocar") 71 and 72 for guiding operation instruments into a peritoneal cavity are inserted into an abdomen of a human body. A meteorismus pneumatics tube 73 is detachably mounted on one of the trocars 72. A high-frequency treatment tool 75 is inserted in an insertion bore 74 in the trocar 72. Further, the endoscope 21 in which the camera head 23 is mounted on the ocular portion 21a is inserted through the other trocar 71 through the camera adaptor 24.

The other end of the insufflation tube 73 is connected to the insufflation device 15. A gas bomb 77 of carbon dioxide or the like is connected to the insufflation device 15 through a gas tube 76. Carbon dioxide gas which is supplied from the gas bomb 77 is controlled by a valve unit 78 and is supplied into the peritoneal cavity 27 from the trocar 72. In this manner, because the carbon dioxide gas is supplied into the peritoneal cavity, the peritoneal cavity is bulged or inflated. An operating space for the operation in the peritoneal cavity is widened or broadened. The field-of-view of the endoscope 21 is also widened or broadened.

The high-frequency treatment tool 75 is electrically connected to an active electrode 80 of the electrical surgical instrument 14 through an active code 79. Moreover, an elastic patient plate (P-plate) 82 formed into a sheet so as to be in intimate contact with skin of the human body is connected to a patient electrode (P-electrode) 81 of the electrical surgical instrument 14. The active electrode 80 and the P-electrode 81 of the electrical surgical instrument 14 are connected to an HF output amplifier 83 which generates high-frequency electric power which is provided within the electrical surgical instrument.

High-frequency current which is outputted from the HF amplifier 83 flows through the active code 79 and the high-frequency treatment tool 75, as shown in FIG. 10. The high-frequency current flows through the human body from the forward end of the high-frequency treatment tool 75, and is returned to the HF amplifier 83 through the P-plate 82. At this time, since a contact area of the high-frequency treatment tool 75 with respect to the human body is small or low, the current density of the high-frequency current extremely increases or rises, and the cellular tissues of the contact portion are evaporated by the high-frequency energy. In this manner, the cellular tissues of the contact portion are successively evaporated, whereby the tissues of the contact portion are excised. Meanwhile, since the contact area of the P-plate 82 is taken broad, the current density decreases so that no change occurs in the cellular tissues.

In this manner, the medical endoscope system which is provided with the plurality of pieces of medical equipment is constructed whereby various treatments can be performed such as performing excision treatment or the like by the electrical surgical instrument, while performing observation of the part to be processed by the endoscope.

Since, in the medical endoscope system 20, the kind or sort of the pieces of medical equipment used increases, these plurality of pieces of medical equipment are accommodated or received in a cart. However, when the number of different kinds of the pieces of medical equipment further increases, these pieces of medical equipment may be installed, dividing or separating into a plurality of carts.

Figure 11:
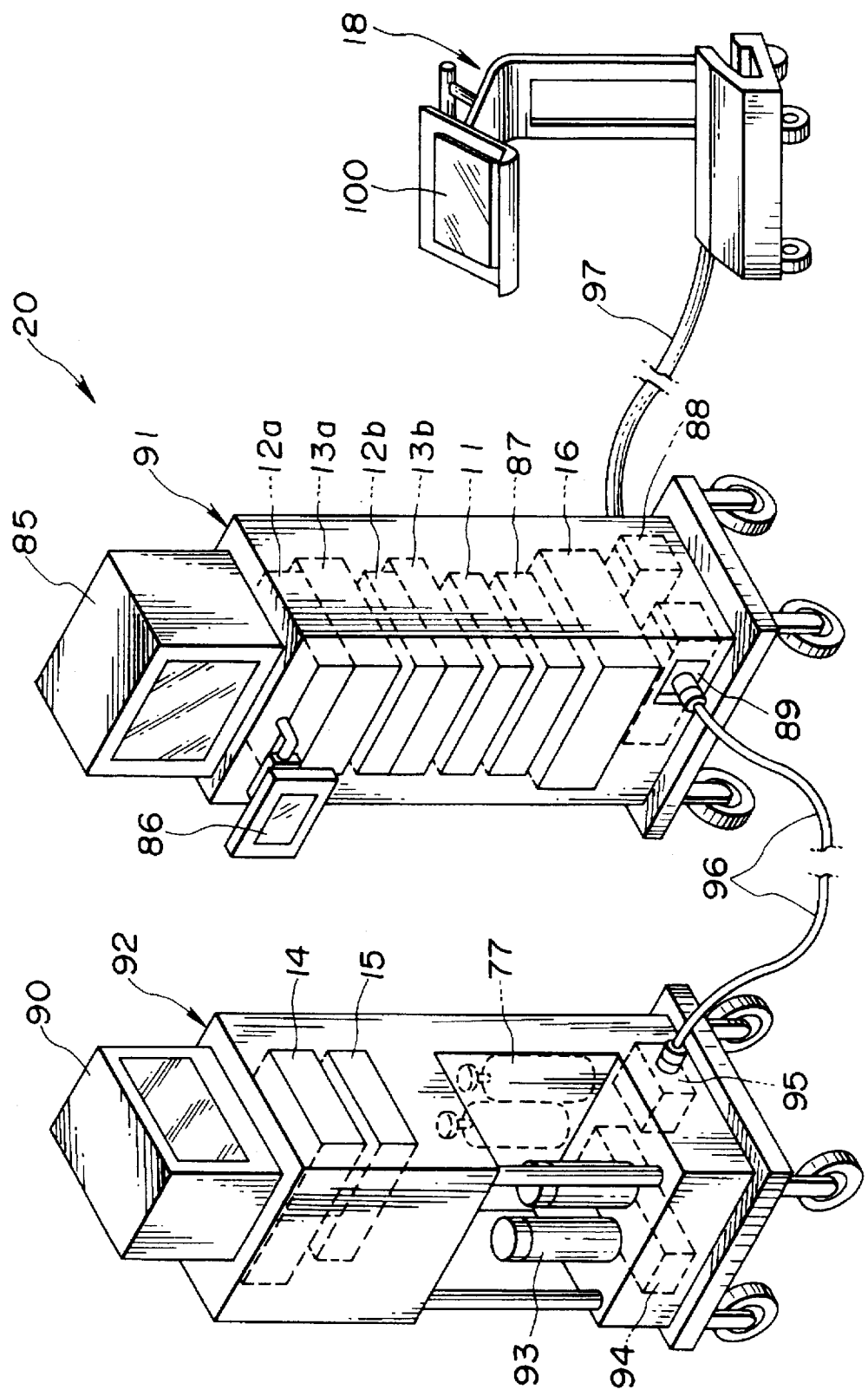

For example, as shown in FIG. 11, the medical endoscope system 20 is arranged such that a first endoscope camera monitor 85, a centralized display panel 86 which is mounted on a cart as the centralized display device 17, a first endoscope camera device 12a, a first camera device light source device 13a, a second endoscope camera device 12b, a second camera device light source device 13b, the system controller 11, a video mixer 87 and the VTR 16 are loaded or taken on a first cart 91 which is provided with a first cart distributor 88 and a communication connector 89, and a second endoscope camera monitor 90, the electrical surgical instrument 14, the insufflation device 15, the CO2 bomb 77 and a suction bottle 93 are loaded on a second cart 92 which is provided with a second cart distributor 94 and a communication connector 95, and the centralized operating device 18 remotely operates these pieces of medical equipment.

The various pieces of medical equipment which are loaded on the first cart 91 are connected, within the cart, to the system controller 11 through a communication cable (not shown) to provide a capability for communicating in a bidirectional manner. Further, the various pieces of medical equipment which are loaded on the second cart 92 are connected, within the cart, to the distributor 94 which is provided on the second cart 92, through a communication cable (not shown). Connection is made to the system controller 11 through a universal cable 96 which builds therein a communication cable which electrically connects the second cart 92 and the first cart 91 to each other, for bidirectional communication. Further, since the centralized operation device 18 and the system controller 11 of the first cart 91 are connected, for bidirectional communication, to each other through a universal cord 97 which includes therein the communication cable, the setting conditions or the operating conditions of all the pieces of medical equipment can be controlled by the centralized operation device 18.

Moreover, the centralized operation device 18 is provided with a display portion and a centralized display panel 100 having operating switches on the display portion.

In this manner, the plurality of pieces of medical equipment are loaded on the cart which is provided with the distributor and the communication connector so that the plurality of pieces of medical equipment are put in order and are arranged without complication within the operating chamber, whereby the plurality of pieces of medical equipment can simultaneously be operated, in a centralized manner, and be controlled. Accordingly, in the endoscope system, there can be produced the operating environments which are suitable for the operator such as the operating doctors, the nurses or the like who perform the operation.

A third embodiment of the invention will be described with reference to FIGS. 12 to 22.

As shown in FIG. 4, the operating panel which performs setting and modification of the setting condition or the operating conditions and which is provided on the pieces of medical equipment, and at least one of the centralized display device 17 provided with the display panel to be described subsequently, serving as the display portion for displaying the setting conditions or the operating conditions of the various pieces of medical equipment and the centralized operation device 18 provided with the centralized display panel 100 are arranged on the medical endoscope system 20.

The centralized display device 17 is one in which the operating doctors who perform the operation see information of the various pieces of medical equipment during the operation. The operating conditions which come into the necessity in the pieces of medical equipment, or the like are displayed in the lump or together on the display panel. Over against this, the centralized operation device 18 has a main or principal object to display the function operating switches or the like to operate the functions to be controlled of the various pieces of medical equipment such that the nurses who take charge of operations of the various pieces of medical equipment and delivery of the forceps or the like in accordance with the instructions of the operating doctors during the operation or the like or the full-time operator can perform operation of the various pieces of medical equipment at a single location.

For this reason, a touch sensor or the like is provided integrally on the centralized display panel 100 such as a liquid-crystal display which is provided as the display portion, or the like. The operating conditions of the various pieces of medical equipment are displayed on the touch sensor or the like, or the function operating switch is displayed on the touch sensor or the like. One touches the touch sensors in which switch electrodes are arranged two-dimensionally on the display regions of these pieces of medical equipment, whereby the function operating switches are operated so that the operating instructions can be performed.

In connection with the above, the system controller 11 is adapted to perform control of the display image planes of the respective panels such that the operating conditions or the setting conditions of the objective pieces of medical equipment are displayed on the respective display panels of the centralized display device 17 and the centralized operating device 18, and objective operational instructions are performed by the centralized operation device 18.

Figure 12:
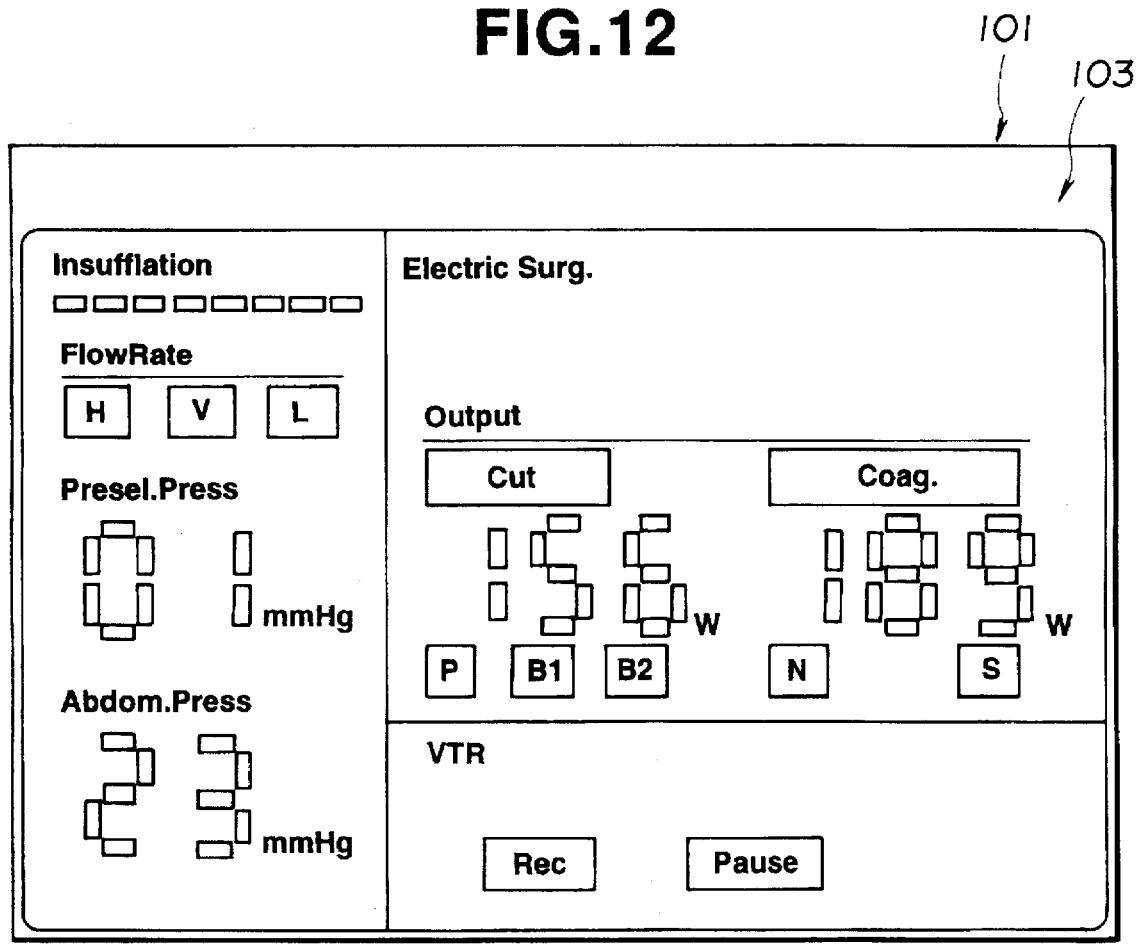
FIGS. 12 to 22 show a third embodiment of the invention, FIG. 12 being an explanatory view showing a display image-plane arrangement of a display panel of a centralized display device.
Figure 13:
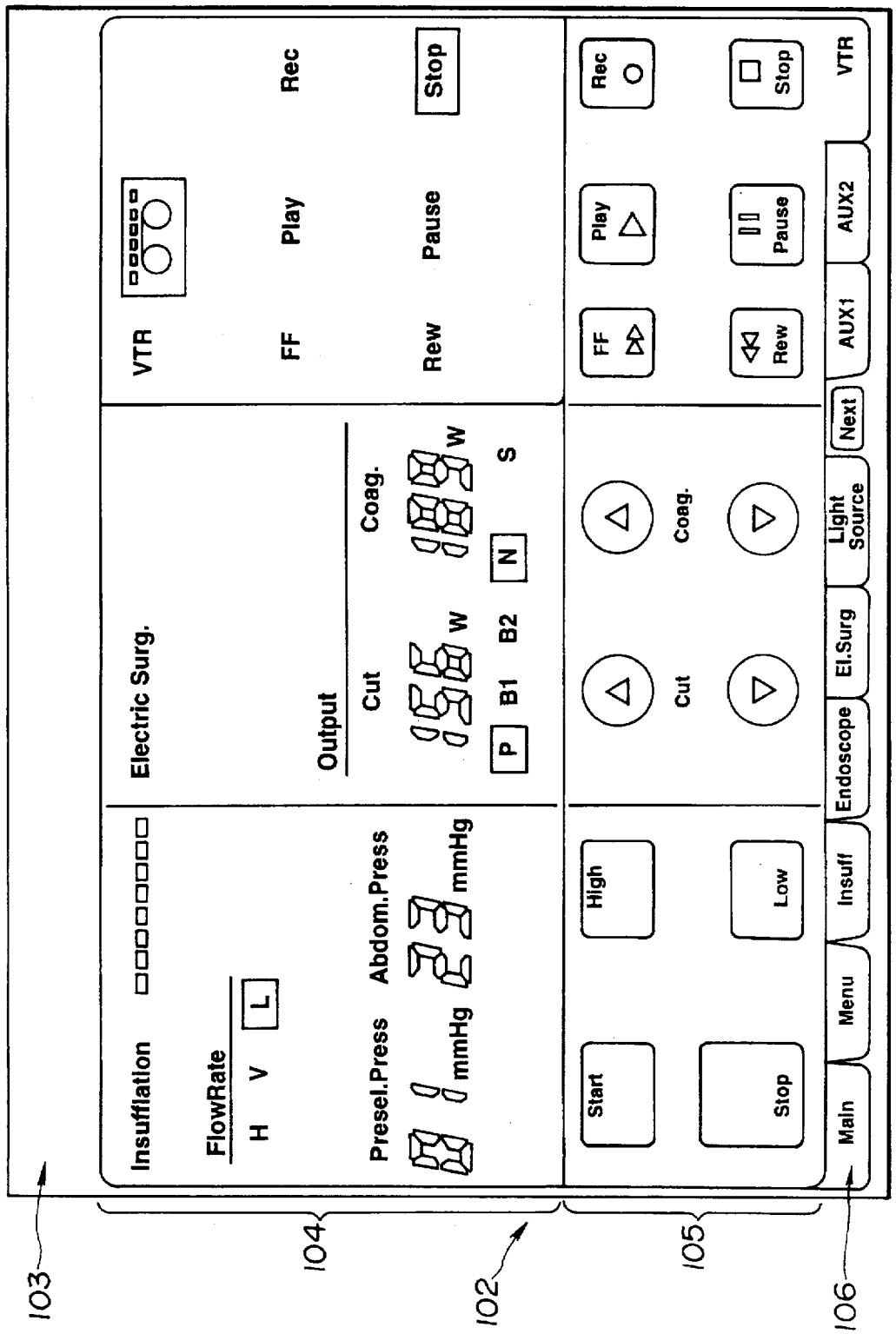

That is, a centralized display image plane 101 as shown in FIG. 12 is displayed on the display panel of the centralized display device 17. A centralized operating image plane 102 as shown in FIG. 13 is displayed on the centralized display panel 100 of the centralized display device 18. Thus, the operating conditions of the objective medical equipment can be viewed in the respective panels, and operation of the objective pieces of medical equipment can be performed by the centralized operation device 18.

Only information which is desired to be mainly or principally watched or monitored by the operating doctor on performing of the operation is displayed on the centralized display image plane 101 of the centralized display device 17, together with information of the operating condition of the medical equipment selected among the medical endoscope system 20, and the like.

On the centralized display image plane 101, the actually measured values of the carbon dioxide gas flow-rate of the insufflation device (Insufflation) 15, the setting value of the abdomen pressure and the actually measured value of the abdomen pressure are displayed on the left-hand side from the above, and the output setting value and the output waveform of the CUT mode of the electrical surgical instrument (Electric Surg.) 14 and the output setting value and the output waveform of the COAGULATION mode are displayed on the right-hand upper side. The video-recording operating condition of the VTR 16 is displayed therebelow.

An idle or free region at an upper end of the image plane is used as an abnormal-content display region 103. In case where an abnormality is detected within the system, the abnormal contents are displayed.

Next, the centralized operating image plane 102 is displayed, in a standard manner, after rising of the power source of the system, in the centralized operation device 18 such that the operating condition of the medical equipment which has a high frequency of use and the function operating switch are displayed among the medical endoscope system 20 such that the nurses and the operators in charge can perform operation of the objective medical equipment in accordance with the instructions of the operating doctor during the operation.

In the centralized operating image plane 102, the contents similar to those of the centralized display device 17 are displayed on an upper-half condition display region 104, while the function operating switch which indicates a switch whose object is the operation is displayed on a lower-half operating switch region 105.

As the function operating switch, the various switches including turning-on and -off of a carbon dioxide gas outflow, abdomen pressure setting, output-level setting in the CUT mode, output-level setting in the COAGULATION mode and operation of the VTR are displayed. If the corresponding display region is depressed, the operating indication or instructions are performed to the corresponding medical equipment.

Figure 14:
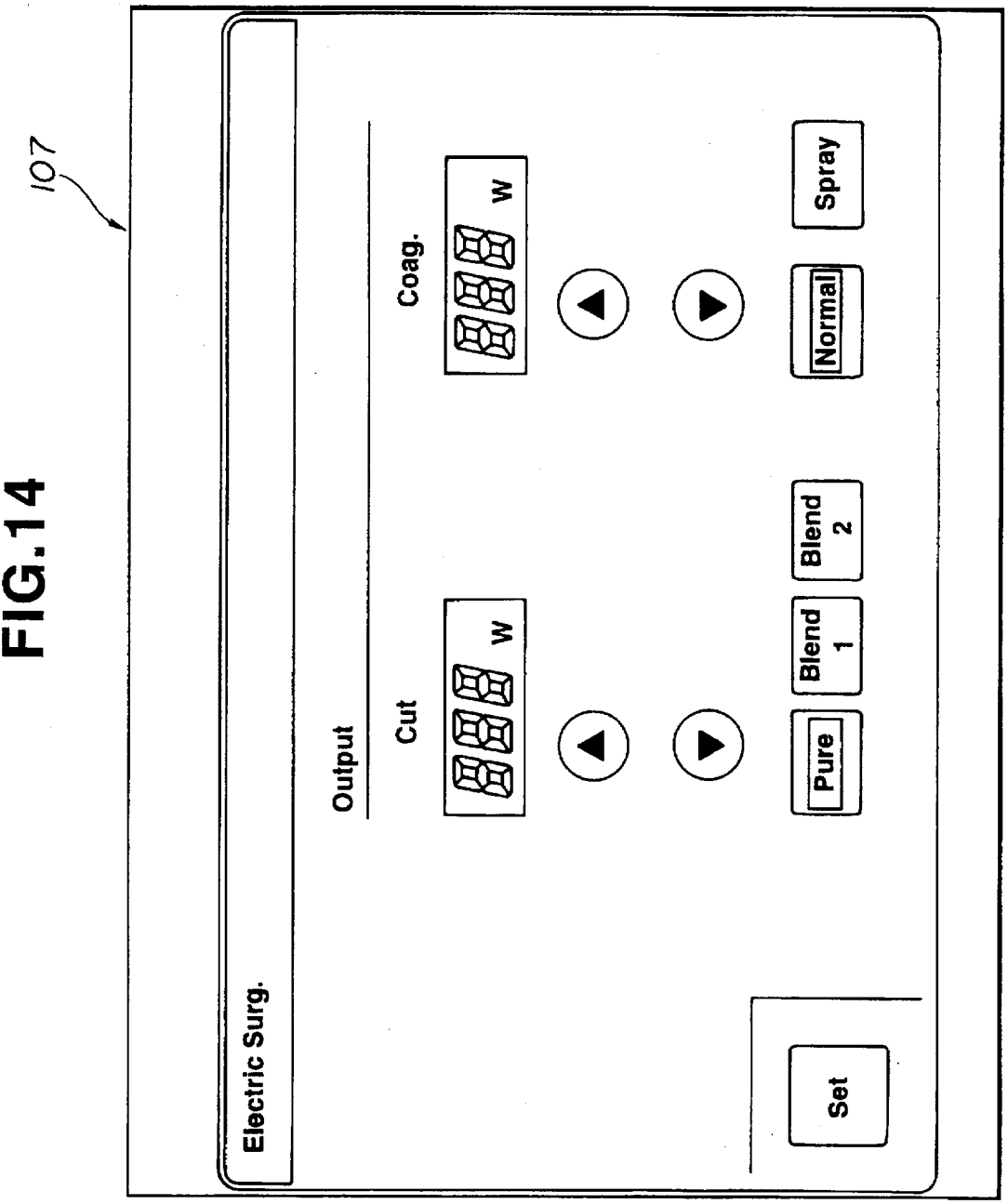

Moreover, the centralized display panel 100 has an operating image plane for the various pieces of medical equipment, which finely operates the various pieces of medical equipment, in addition to the centralized operating image plane 102. A priority level is applied to the operating image planes for the various pieces of medical equipment, depending upon the frequency of use of the pieces of medical equipment, and these operating image planes are arranged as hierarchy image planes in accordance with the priority level. For this reason, a tag-switch display portion 106 for calling or invoking a desired operating image plane of the pieces of medical equipment is provided at a lower end of the hierarchy image plane. By the fact that the tag-switch display portion 106 is depressed, the image plane is changed to an image plane of the corresponding pieces of medical equipment. For example, by the fact that "El. Surg." within the tag-switch display portion 106 in FIG. 13 is depressed, an electrical-surgical-instrument operating image plane 107 shown in FIG. 14 is displayed on the centralized display panel.

In this manner, the plurality of image planes are made to a hierarchy image plane arrangement, whereby the functions to be controlled of all the pieces of medical equipment which arrange the medical endoscope system can be displayed on the limited display panel, irrespective of more or less of the connected medical equipment.

Furthermore, in the endoscope system in which the plurality of pieces of medical equipment are used simultaneously, at least one of the centralized display devices which selects the display object and the centralized operation device which is provided with the display portion is provided as display means. The information contents which are required by a person who mainly uses the information contents are individually displayed on the respective display image planes every display portion. Accordingly, unnecessary display decreases at the display portions, and display which has no waste and which is high in visibility can be performed. Thus, complication of the operation can be prevented from occurring, and the operating condition of the objective medical equipment can easily be grasped.

A notice or notifying method at the time abnormality is generated in the medical endoscope system will next be described.

Regarding the abnormality in which continuation of the operation is possible such as lamp running-out of the light source or the like (since an auxiliary lamp is provided on the endoscope light source device 13), or the like, the abnormal contents are displayed on the abnormal content display region 103 at the upper end of the image plane, on the centralized display device 17 and the display panel of the centralized operating device 18.

Figure 15:
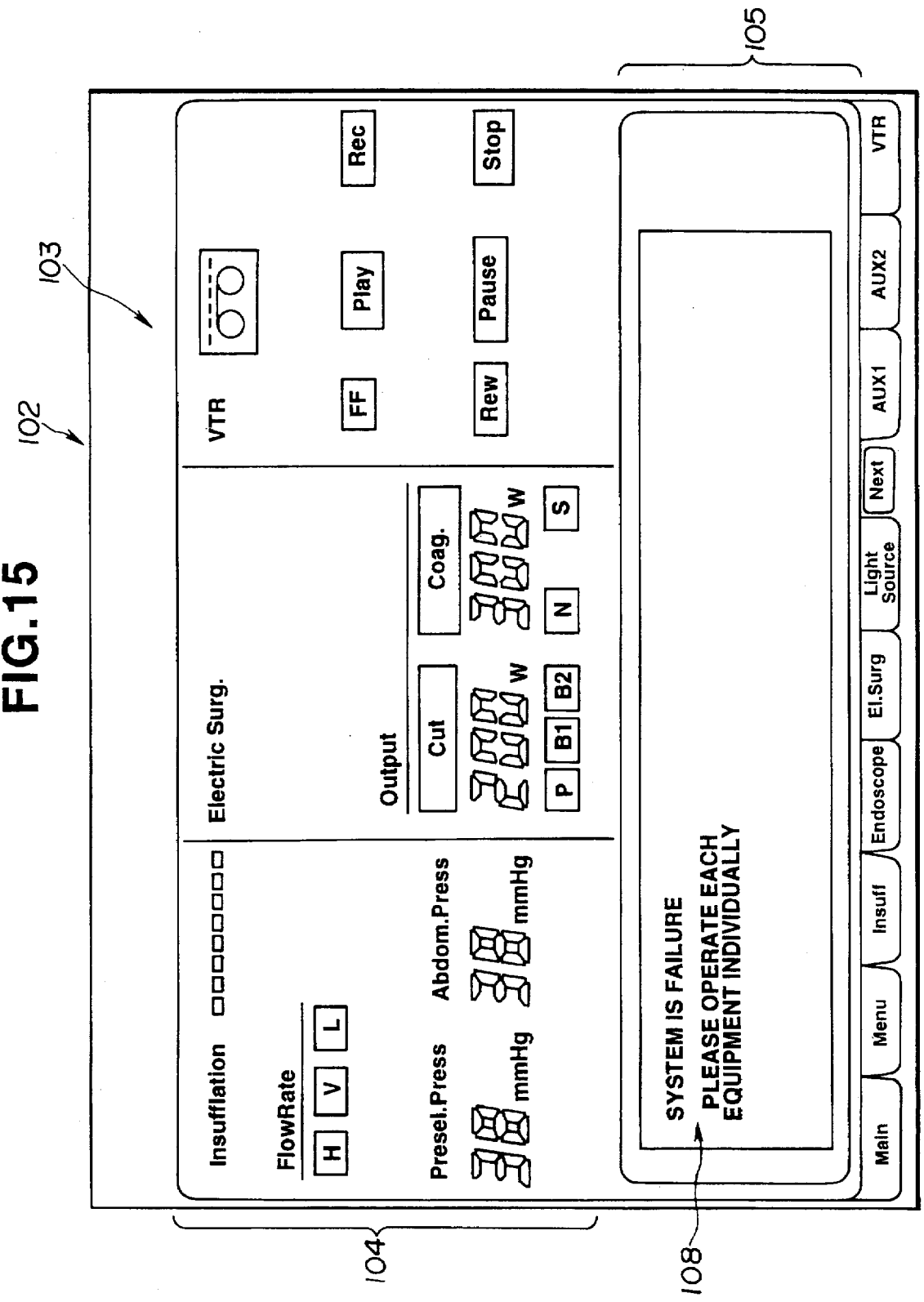

Meanwhile, regarding an important abnormality such as communication failure, the abnormal display 108 is largely displayed on the operating switch region 105 in the centralized operating device 18, as shown in FIG. 15.

In connection with the above, since the various pieces of medical equipment which form the system are arranged such that the control from the operating panels which are provided in the respective pieces of medical equipment are set the highest in priority order rank or level, even in case where, by any chance, the control signal regarding the system control comes into service interruption or suspension, control of the various pieces of medical equipment can be performed through the console panel.

Figure 16:
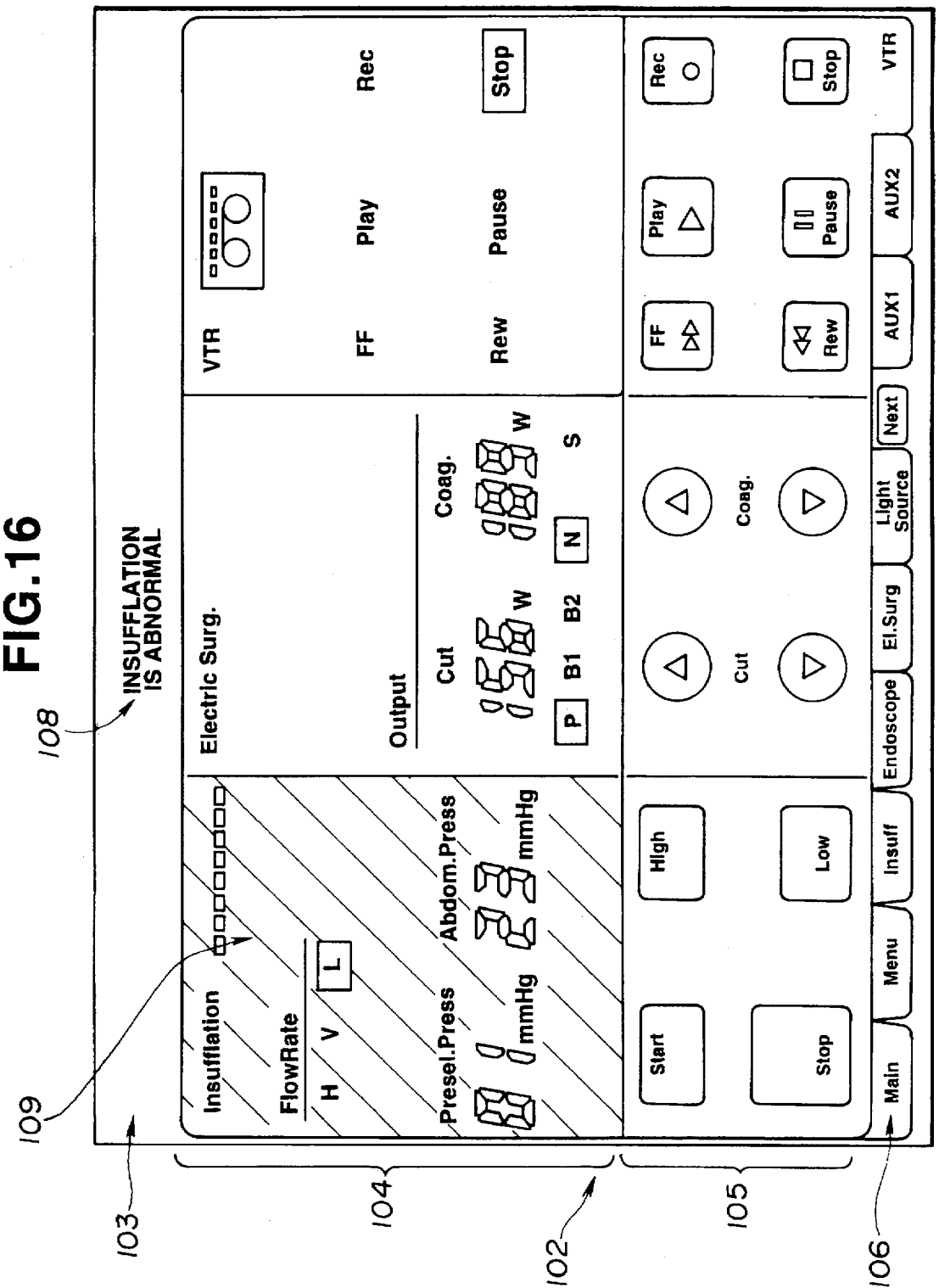

Further, it is required or necessary to display the abnormal display 108 which indicates the abnormality of the pieces of medical equipment on the image plane and to accurately or precisely notify, at a moment's notice, how and in what piece of medical equipment the abnormality is generated. Accordingly, as shown in FIG. 16, whenever the abnormality is generated in any one of the pieces of medical equipment during system control, an error signal is transmitted to the system controller 11 from the medical equipment. The abnormal contents are displayed on the abnormal content display region 103, and the display region of the medical equipment in which the abnormality is generated is reversely displayed. In the present figure, it is notified that the abnormality occurs in the insufflation device 15, by an abnormal display 108 and the reverse display of a display region 109.

Figure 17:
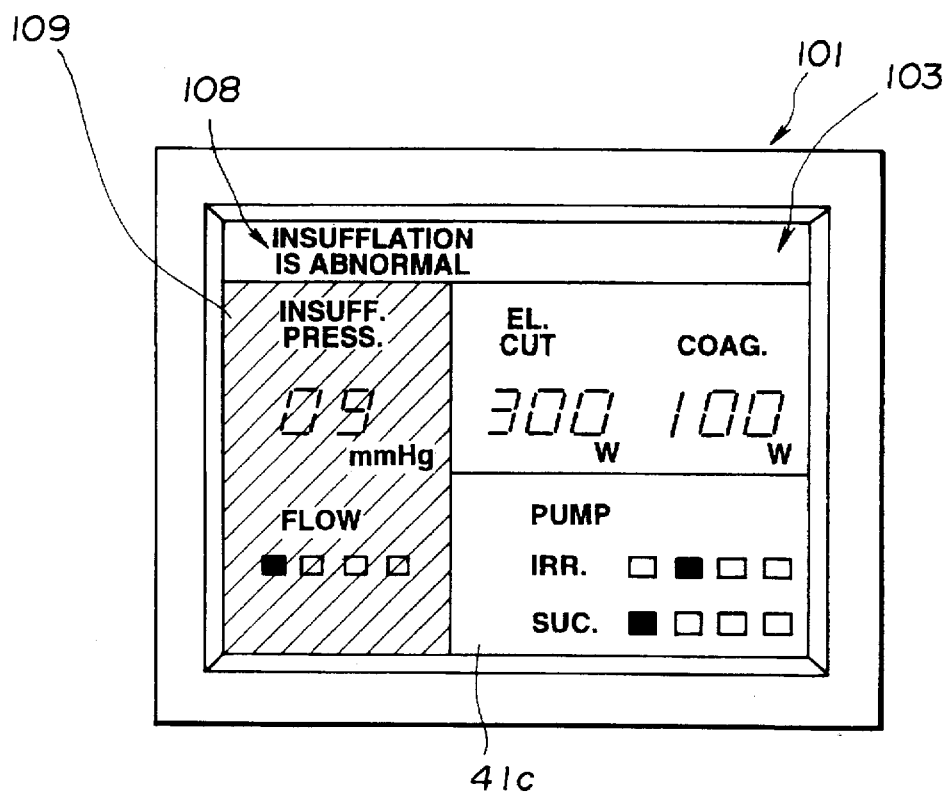
Figure 18:
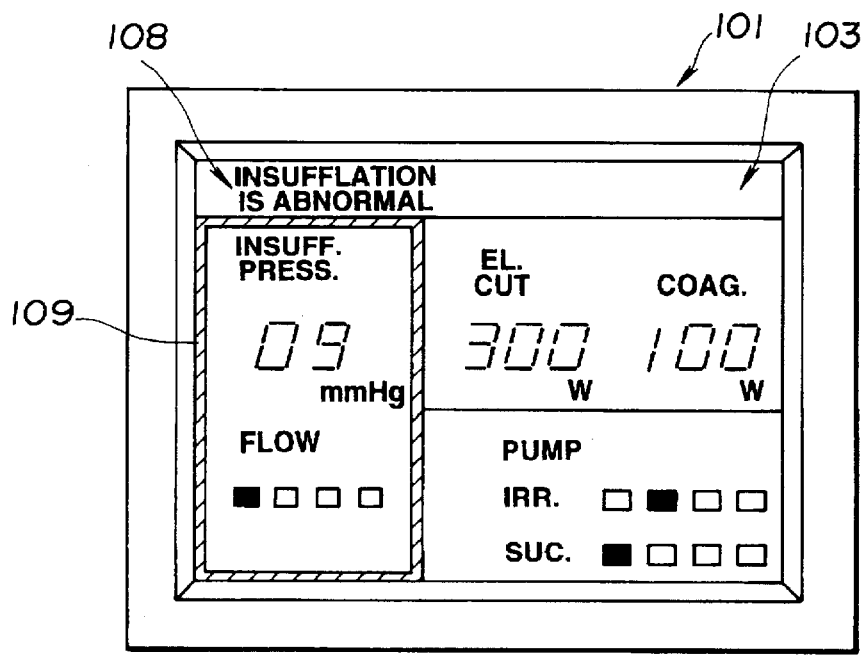

In connection with the above, the notifying method of the error equipment should not be limited to the reverse display. As shown in FIG. 17, the arrangement may be such that the abnormal display 108 is performed, and the display region 109 is turned on (turned-on and -off), and the color tone is changed. Moreover, the arrangement may be such that, as shown in FIG. 18, the abnormal display 108 is performed, and notification is made by the fact that a frame is applied to the display region 109.

Figure 19:
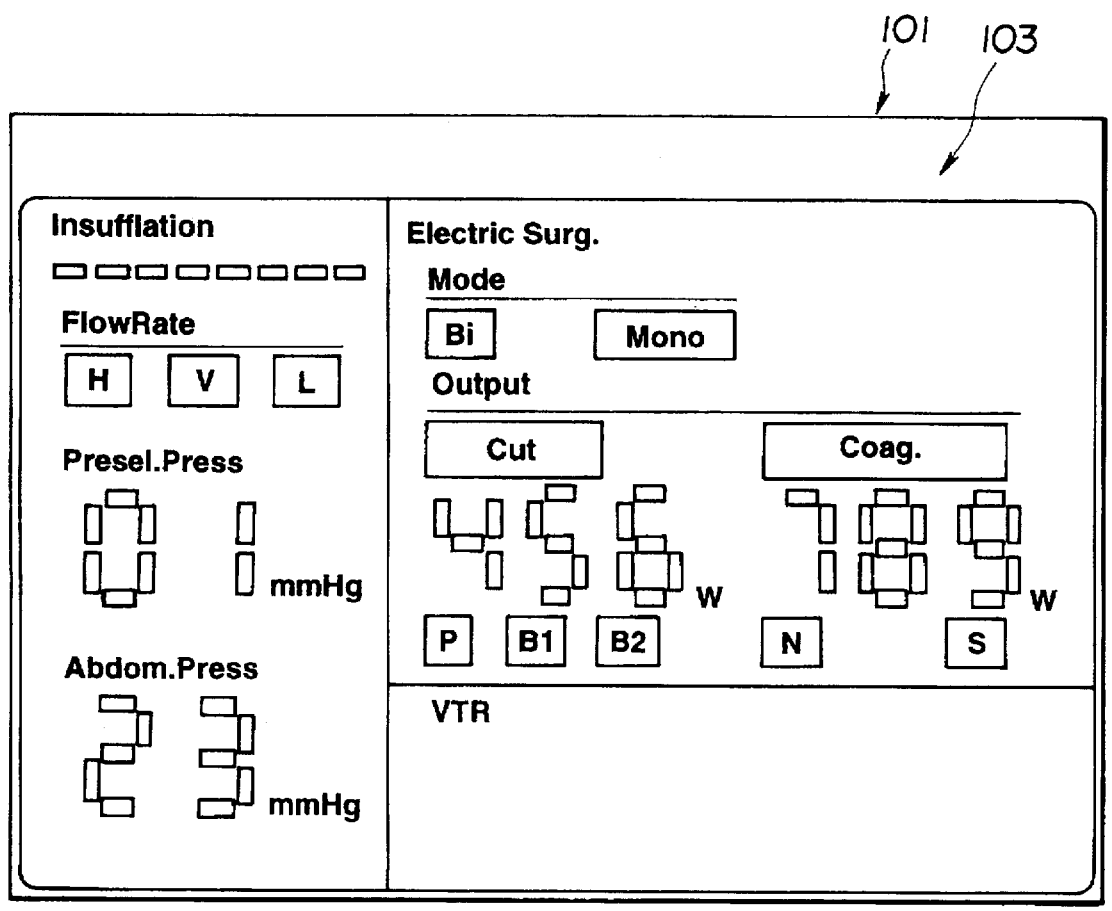

Furthermore, in case where connection failure occurs between the pieces of medical equipment and the system controller, in order, for example, to notify the operator that bidirectional communication is not performed between the system controller 11 and the VTR 38, as shown in FIG. 19, operating display of "REC" and "PAUSE" which indicates the operating condition within the display region of the VTR 16 of the centralized displaying image plane 101 which is displayed on the display panel of the centralized display device is excepted.

Figure 20:
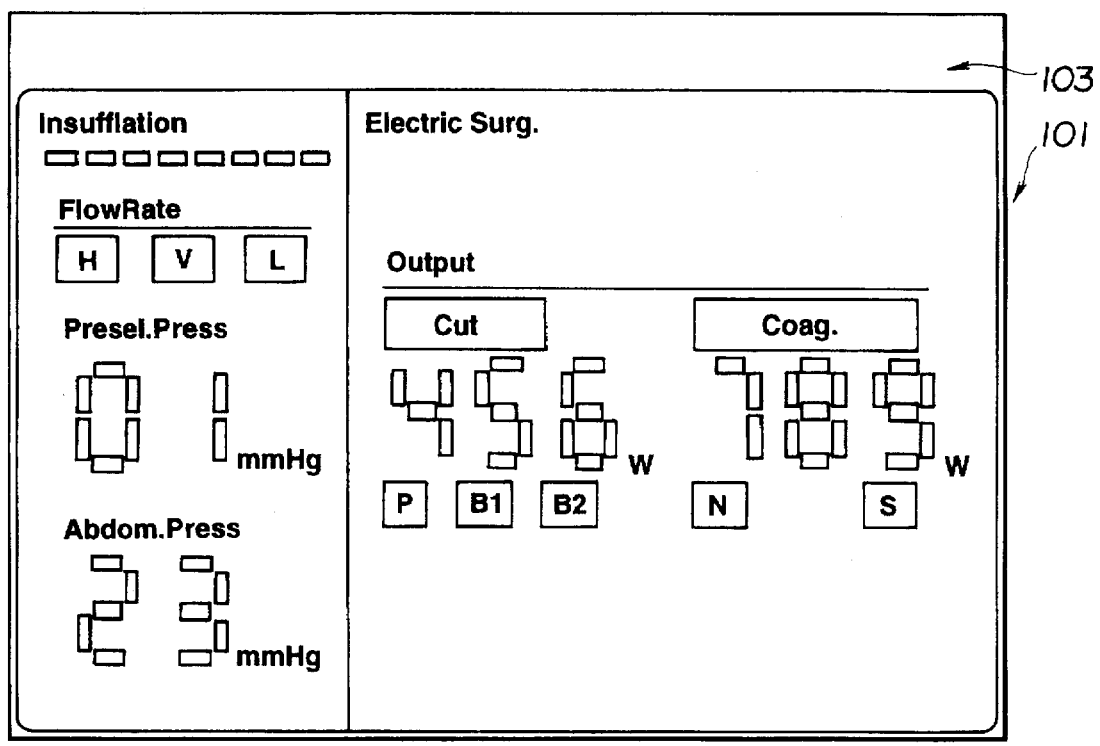
Figure 21:
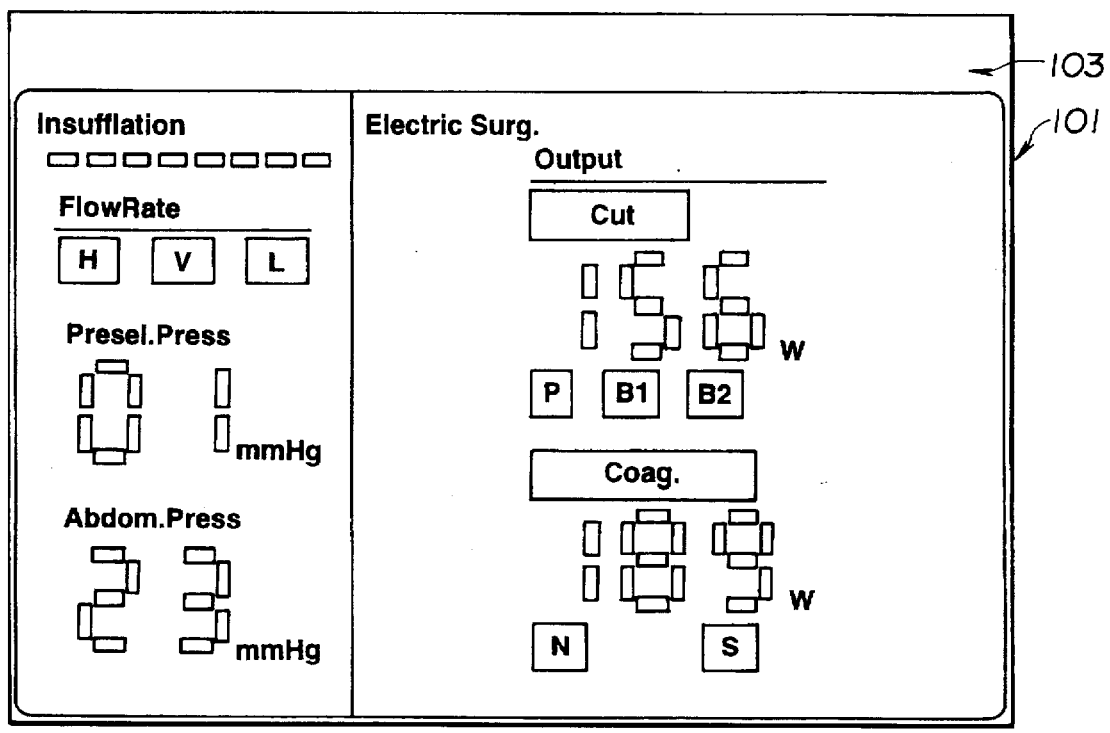
Figure 22:
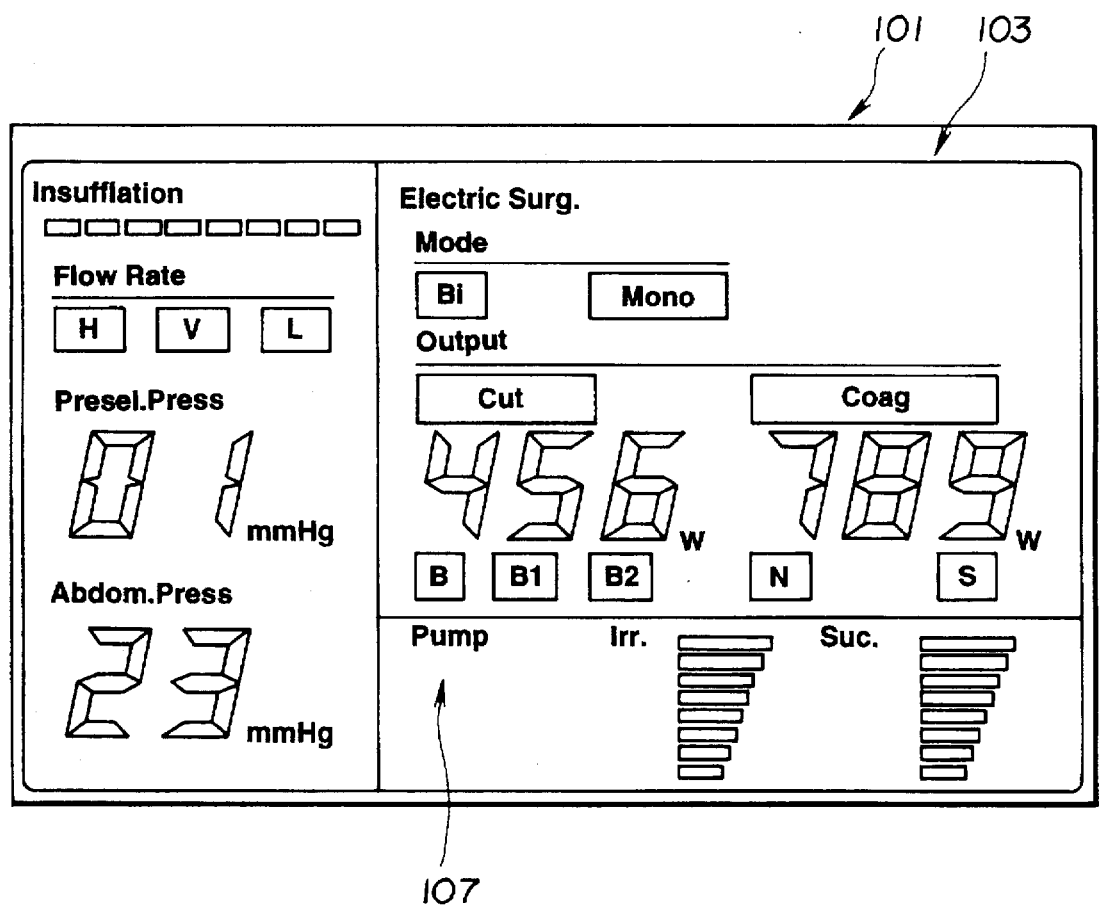

In connection with the above, the notifying method of the connection failure should not be limited to the fact that the operating display of the operating condition is excepted. The arrangement may be such that, as shown in FIG. 20, the display region of the medical equipment (VTR in the present figure) which is not connected is erased from the display image plane, in case, as shown in FIG. 21, where there is a connection failure in the pieces of medical equipment which is displayed on the centralized display device 17, display is not performed with respect to the pieces of medical equipment which are not connected, and display of the other pieces of medical equipment which are connected is performed by the effective use of the empty or unoccupied region. In the present figure, when the VTR 16 is not connected, display of the operating condition of the electrical surgical instrument (Electric Surg.) 14 is assigned or allocated to the region of "VTR" in the display image plane so that the display portion of the electrical surgical instrument 14 is so arranged so as to be wide and as to be easy to be seen. Further, as shown in FIG. 22, display of the other pieces of medical equipment, for example, a pump (Pump) 107 whose priority level is positioned next may be performed on the display region of "VTR".

In this manner, when the error is generated in the plurality of pieces of medical equipment within the medical control system, abnormal information can be provided, at instance, to the operating doctors, or the nurses, the operators or the like, by the error message and the visual sense display, while anxiety or uneasiness is not given to the patent by warning sound or the like. Moreover, when there is a failure in the connection status between the pieces of medical equipment, the display of the equipment which have a failed connection is removed or excepted partially or all from the display image plane, whereby the operators can recognize, on a moment's notice, that there is a connection failure in the system. Accordingly, misunderstanding such as the fact that the connecting condition is erroneously recognized can be eliminated.

In connection with the above, in case where, in the medical endoscope system, there are the pieces of medical equipment which are not connected in the pieces of medical equipment to be displayed on the centralized display device, and the medical equipment which is low in priority is connected in the system, as described previously, display regarding the medical equipment which is next highest in priority order or level may be performed, in carrying-up, on the centralized display device. Further, a similar function may be had by the centralized display panel of the centralized display device, not limited to the centralized display device.

Meanwhile, in the hierarchy image plane which is displayed on the centralized display panel of the centralized display device, there is a backup setting image plane which sets the contents performed in backing up the user, as one for desired operating setting of the functions of the various pieces of medical equipment in the medical endoscope system.

The backup setting image plane is one in which the user can back up the contents of a part of the functions of the various pieces of medical equipment, as the desired operating setting, because, in the system which is provided with the plurality of pieces of medical equipment, in case where the system rises, the system crashes, or the like, if all the pieces of medical equipment are returned to the initial condition, it becomes troublesome setting or producing the desired operating condition. In the present embodiment, the contents of such backup are capable of being selected, and the operability is improved.

Figure 23:
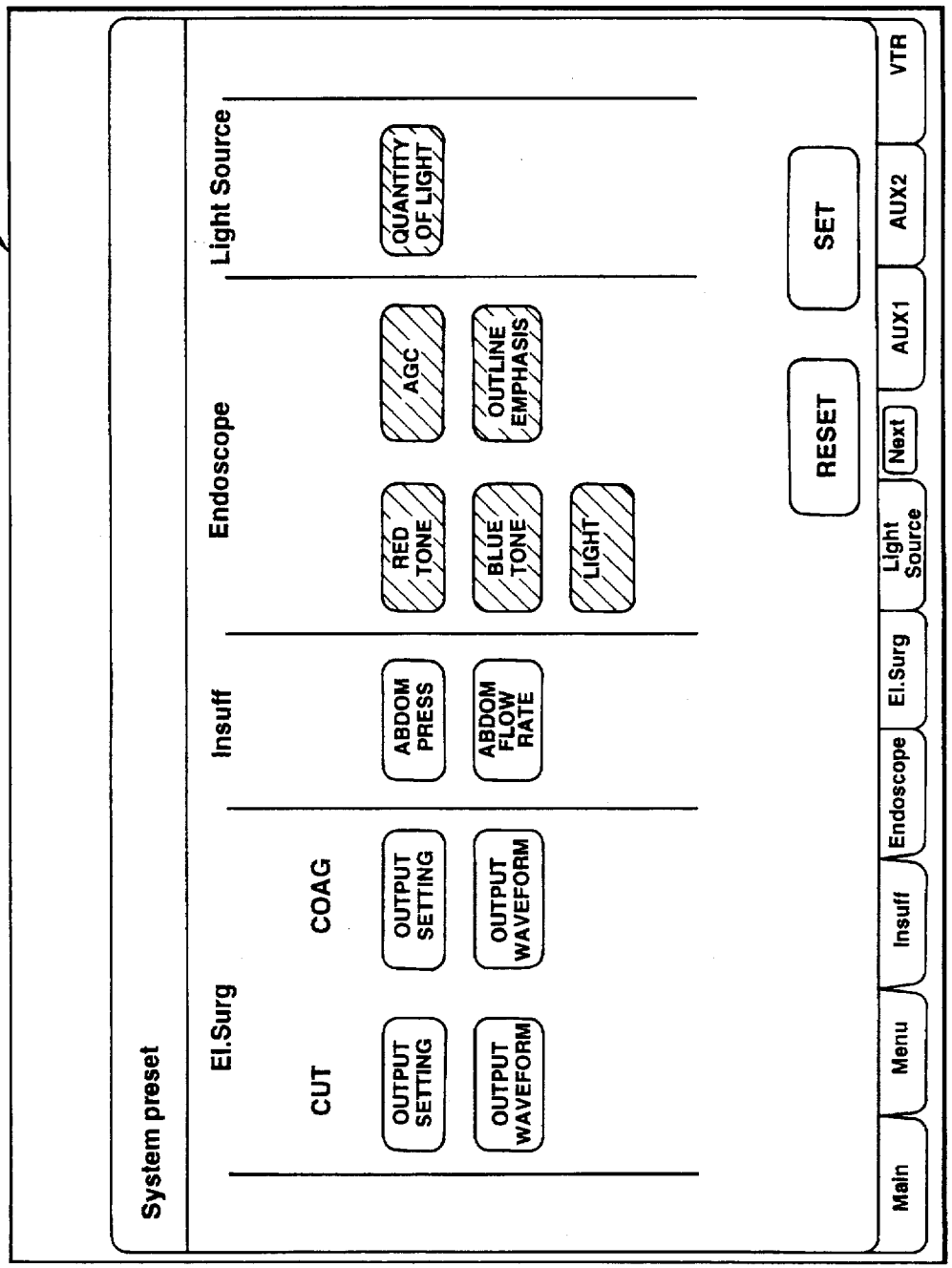
FIG. 23 is an explanatory view showing an arrangement of a backup image plane.

When the backup setting operation is performed, a backup setting image plane 99 shown in FIG. 23 is displayed on the centralized operation device 18. The backup setting image plane 99 is such that a tone of color of the display portion of the key portion corresponding to the contents which normally are backed up, for example, is shown or indicated in changing like items of "endoscope camera" and "light source" in the present figure. (In the present figure, the key portion is indicated by slash to express that the display portion is changed.)

Next, in case where the items which are backed up are changed or modified, when a "RESET" key on the right-hand lower position of the image plane is depressed, key tops which correspond to the items which are backed up till the eve thereof start turning-on and -off. In the present figure, keys corresponding to the various items of "endoscope camera" and "light source" are turned-on and -off. Here, if the key of "quantity of light" of the light source which is turned-on and -off, for example, is again depressed, the turning-on and -off operations stop. Changing is made to the display condition the same as that of the key of the item which is not backed up. When the key is again depressed, turning-on and -off operations begin. Under the condition, when a "SET" key on the right-hand lower of the image plane is depressed, the items of the keys which are turned-on and -off such as "quantity of light" or the like are again set as items which are backed up. That is, in this case, consequently, the item the same in content as the original one is backed up.

In this manner, out of the functions of the respective pieces of medical equipment in the system, the items which are backed up by the system are made selectable, whereby the items which are always made to the same desired setting are registered upon the use of every one of the operators. Accordingly, it is possible to omit the time and trouble required for setting up of the system. Thus, the operability of the system is considerably improved.

In connection with the above, the items regarding whether or not the backing up is performed should not be limited to ones indicated in the figure. Even the functions of the pieces of medical equipment which form the system are also applied as the backing-up items similarly.

A fourth embodiment of the invention will be described with reference to FIGS. 24 to 30.

Figure 24:
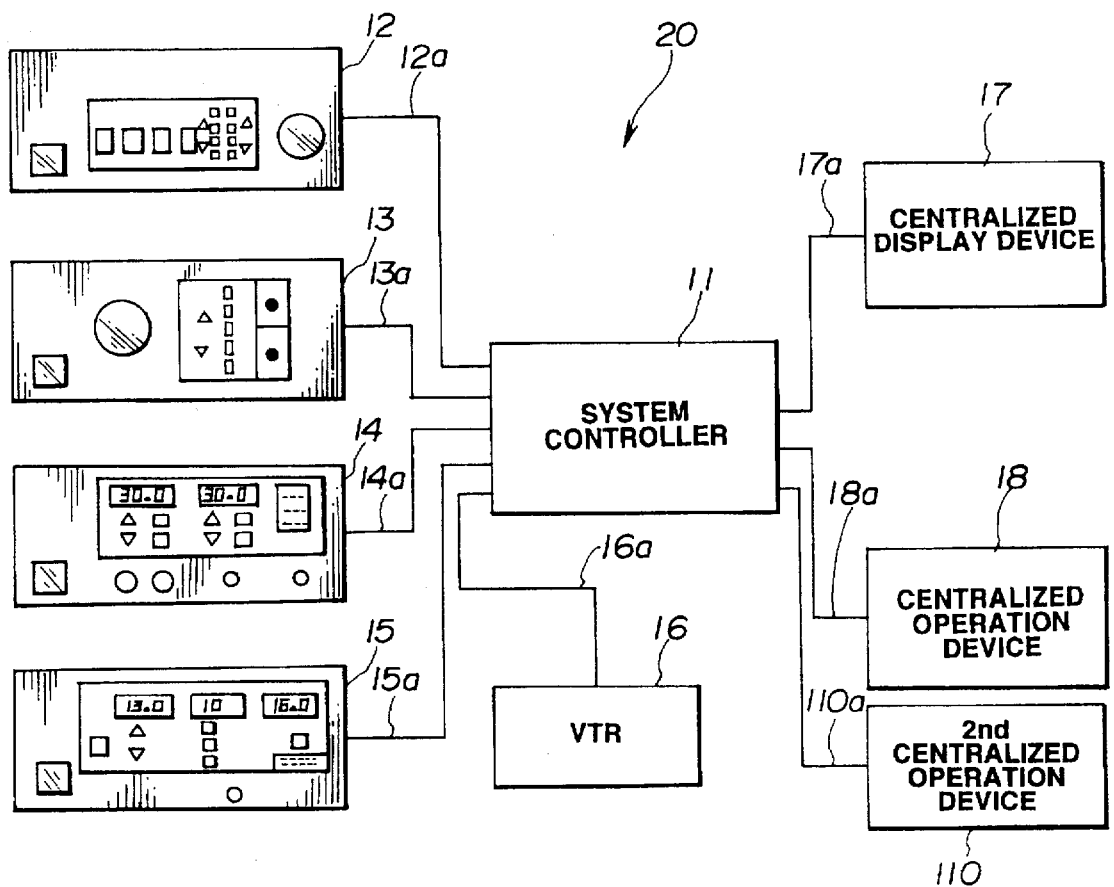

The present embodiment is an example which is arranged such that, as shown in FIG. 24, a second centralized operation device 110 is connectable to the system controller 11. The arrangements of the centralized display panels or the like of the centralized display device 17 and the centralized operation device 18 are similar to those of the third embodiment. Here, only different portions will be described.

Figure 25:
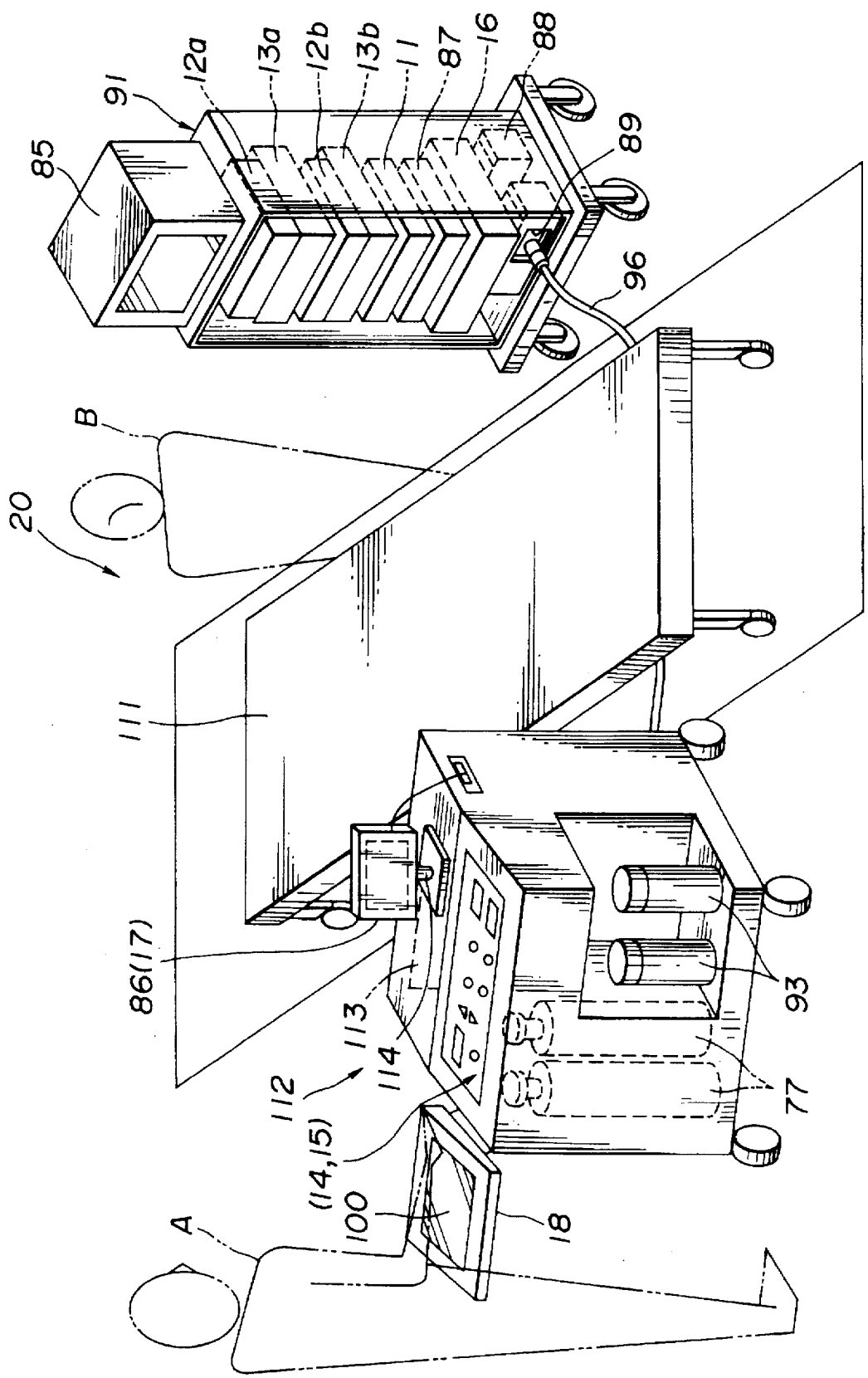

As shown in FIG. 25, the interior of the operating chamber is divided into a sterile area in which only sterilized ones can be placed, centering around a position of an operation table 111 on which the patient lies down, and an unsterile area which is positioned around the sterile area. In the present embodiment, in the medical endoscope system 20, all the pieces of medical equipment which are loaded on the cart 91 which is handled by the nurses, the operating doctors A or the like, and an endoscope operation unit 112 formed as a unit which has, in combination, the electrical surgical function, the insufflation function and the pump function, the centralized display device 17, the centralized operation device 18 or the like are installed on the unsterile area, except that only the second centralized operation device 110 which is operated by an operating doctor B is arranged out of the sterile area.

The endoscope operating unit 12 has a connector group 113, the display panel 86 serving as the centralized display device, and the centralized display panel 100 serving as the centralized operation device. The endoscope operating unit 112 is capable of being used as an endoscope operating unit, without being connected to the pieces of medical equipment which are loaded on the first cart 91. When the endoscope operating unit 112 is used as a unit, only functional information with which the endoscope operating unit 112 is provided is displayed on the centralized display panel 86. Meanwhile, whenever the endoscope operating unit 112 is electrically connected to the first cart 91 through the system controller 11 which is loaded on the first cart 91, functional information of the pieces of medical equipment which are required, of the plurality of pieces of medical equipment which are loaded onto the first cart 91 is also displayed on the centralized display panel 86 together. In this connection, the centralized display panel 86 is angularly movable with respect to a shaft 114 which is provided on the endoscope operating unit 112.

Upon performing the operation, the operating doctor B cannot touch ones which are positioned in the unsterile area naturally in the meaning to prevent infection. For this reason, whenever the operating conditions of the respective pieces of medical equipment are changed during operation, instructions must be sent to an operational person A in charge which is in the unsterile area. However, since checking of the pieces of medical equipment must be performed also during the operation on the side of the unsterile area, the operating person in charge A is not necessarily limited to reside at a location of the centralized operation device 18. Further, there is a fear that the operating doctor B may not always send instructions to the operating person in charge A in time when the operation is an emergency operation. In view of this, a second centralized operation device 110 is provided as a centralized operation means on the assumption of the use in the sterile area, such that the pieces of medical equipment can be operated by the operating doctor B per se.

FIG. 26 shows the disposition arrangement of the second centralized operation device 110, the function operating switches thereof or the like. As shown in FIG. 26, only the functional switches of the pieces of medical equipment which are frequently operated during operation are arranged together on the second centralized operation device 110. In FIG. 26, various switches including abdomen pressure setting, abdomen flow-rate setting, output-level setting in a CUT mode, output-level setting in a COAGULATION mode, and video recording of a VTR are provided substantially similarly to the operating switch region 105 of the display image plane of the centralized operating device 18 shown in FIG. 13.

Accordingly, the plurality of pieces of medical equipment which are provided in the medical endoscope system 20 are controllable by one of the centralized operation device 18 and the second centralized operation device 110.

In connection with the above, also in the present embodiment similar to the second embodiment, control from the console panels which are provided on the respective pieces of medical equipment is made possible, and the control priority for controlling the various pieces of medical equipment is as follows in order:

Operating portions of respective pieces of medical equipment>Second centralized operation device>Centralized operation device However, when the plurality of pieces of medical equipment are operated by two operating devices including the centralized operation device 18 and the second centralized operation device 110, it is considered that the control signal for controlling the functions of the different pieces of medical equipment substantially simultaneously (within a predetermined period of time t sec.) from the centralized operation device 18 and the second centralized operation device 110, or the control signal which intends to perform the contrary controls with respect to the functions of the same pieces of medical equipment is inputted to the system controller 11.

For this reason, it is considered that there exist mixed together, in the system controller 11, the control signals from the centralized operation device 18 and the second centralized operation device 110 substantially simultaneously, that is, the control signals which intend to perform contrary controls with respect to the functions of the same devices within the predetermined period of time of t seconds.

In view of the above, as shown in FIG. 27, the operating signal pulse which is outputted from the centralized operation device 18 and the second centralized operation device 110 includes three (3) stages including communication start (rising portion), a communication period of time (parallel line portion), and communication completion (rising portion), and the contents of the operating signals are unknown until the communication is completed. Accordingly, before the predetermined period of time t seconds elapses from the moment that the control signal is inputted to the system controller 11 from the centralized operation device 18, a control signal contrary to the control signal which is outputted from the centralized operation device 18 is inputted to the system controller 11 from the second centralized operation device 110. Whenever two signals reside mixed together within a predetermined period of time, only the control signal from the second centralized operation device 110 which is high in control priority level is processed. Thus, for example, whenever a "DOWN" switch of the abdomen pressure of the insufflation device is depressed at the second centralized operation device 110 within the predetermined period of time t seconds from the moment that the "UP" switch of the abdomen pressure of the insufflation device is depressed at the centralized operation device 18, and the control signals are inputted simultaneously, the control signal from the second centralized operation device 110 which is operated by the operating doctor has priority so that control of the abdomen pressure "DOWN" of the insufflation device is performed.

Further, as shown in FIG. 28, whenever the control signal contrary to the control signal which is outputted from the centralized operation device 18 is under communication from, for example, the second centralized operation device 110 to the system controller 11 when the predetermined period of time t sec. has elapsed from the moment the control signal has been inputted to the system controller 11 from, for example, the centralized operation device 18, the plurality of control signals which have been finished or completed in communication do not reside mixed together. Accordingly, the control signal from the centralized operation device 18 which is inputted previously is processed and, subsequently, the control signal from the second centralized operation device 110 is processed.

Moreover, as shown in FIG. 29, whenever the control signal contrary to the control signal which is outputted from the second centralized operation device 110 is inputted to the system controller 11 from the centralized operation device 18 before the predetermined period of time t sec. elapses from the moment that the control signal has been inputted to the system controller 11 from the second centralized operation device 110, and two signals reside mixed together within the predetermined period of time, only the control signal from the second centralized operation device 110 which is high in control priority level is processed.

Furthermore, as shown in FIG. 30, whenever the control signal contrary to the control signal which is outputted from the second centralized operation device 110 is under communication to the system controller 11 from the centralized operation device 18 when the predetermined period of time t sec. has elapsed from the moment that the control signal has been inputted to the system controller 11 from the second centralized operation device 110, a plurality of signals do not reside mixed together within the predetermined period of time. Accordingly, the control signal from the second centralized operation device 110 which is inputted previously is processed and, subsequently, the control signal from the centralized operation device 18 is processed.

Meanwhile, whenever control signals which control different functions of the pieces of medical equipment are inputted to the system controller 11 from the centralized operation device 18 and the second centralized operation device 110, within the predetermined period of time t, the control signals are processed in accordance with the order of being inputted.

In connection with the above, in the figure, the starting point of the predetermined period of time t is the time of falling which means completion of communication of the communication pulse. However, the start point of the predetermined period of time t should not be limited to the time of completion of communication. The start point of the predetermined period of time t may be the time of rising which means start of communication of the communication pulse. At this time, the predetermined period of time t comes into the time to which the pulse duration is added.

According to the present embodiment, in the system which has the plurality of control input devices, the control priority level is applied to the device which can perform control input, whenever indicating or instruction contents contrary to each other with respect to the single function are inputted within the predetermined period of time from the respective control input devices, processing is performed in accordance with the control priority level.

Further, since the operating instructions from the operating portions of the various pieces of medical equipment are set first in the priority level, in case where abnormality is generated, by any chance, in the present medical endoscope system so that control by means of the second centralized operation device or the centralized operation device is made impossible, the console panel which is provided in the pieces of medical equipment are operated whereby the operation can smoothly be continued without confusion of the operation.

Moreover, the operating doctor who becomes skilled in the technique of the operation operates the second centralized operation device which is high in control priority level, whereby, whenever an inadequate operating indication or instructions are performed from the centralized operation device which is operated by the nurses or the like, the condition can immediately be returned to an adequate condition by the operating doctors who operate the second centralized operation device.

Furthermore, the centralized operation device which is capable of operating all the functions to be controlled of the pieces of medical equipment which form the system, and the second centralized operation device which operates the functions to be controlled which are often used are provided within the system, whereby the necessity that one specially visits the various pieces of medical equipment in order to operate the various pieces of medical equipment is eliminated and, accordingly, the possibility that the sterile area is contaminated is considerably reduced. Even where the operating person in charge is, by any chance, far away from the centralized operation device, the main or principal pieces of medical equipment should be operated by the second centralized operation device. Thus, the operation proceeds more smoothly. The other functions and advantages are similar to those of the third embodiment.

In connection with the above, although the setting of the predetermined period of time is after t seconds as measured from the start of communication, the setting of the predetermined period of time may be after t seconds from the start of communication.

Further, since the image plane of the centralized display panel of the endoscope operating unit 112 indicated in FIG. 25 is movable angularly, the centralized display panel 86 is always opposed against the operating doctors, whereby the operating doctors can easily view the display contents of the centralized display panel 86 within the sterile area.

By the way, if a liquid-crystal display of a flat type is used as the display panel, it is difficult to adjust or regulate the display image plane of the display panel to a position which may be easily seen, because an angle of a field-of-view is narrow. Particularly, it has been impossible to set an attack angle of the display image plane at a preparation stage in which display is not performed on the display image plane.

Figure 31:
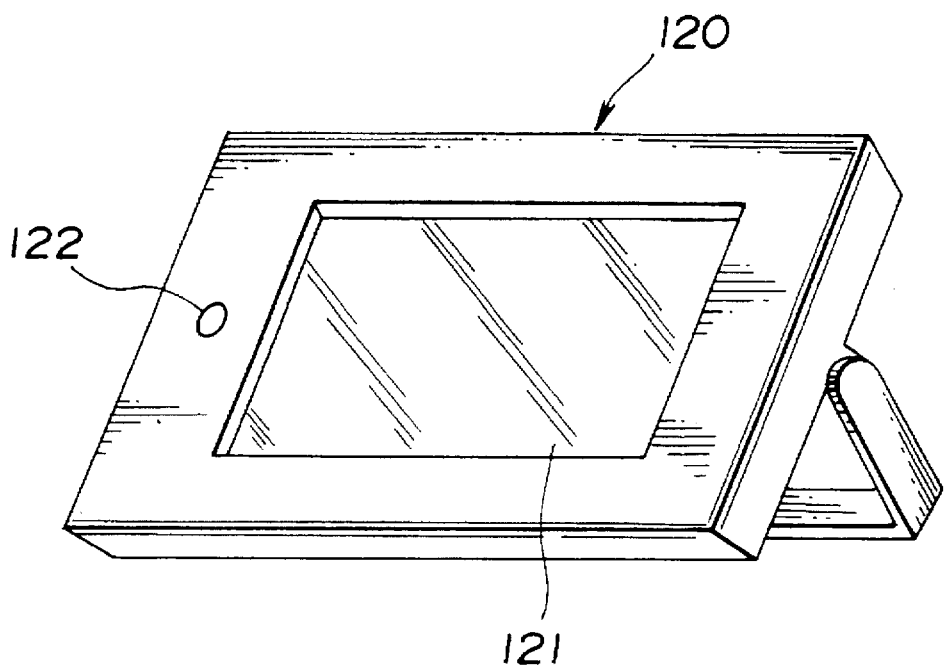
FIGS. 31 to 34 show a fifth embodiment of the invention, FIG. 31 being a perspective view of a display panel provided with angle adjustment means on a planar portion which is the same as or coplanar with an image display portion.
Figure 32:
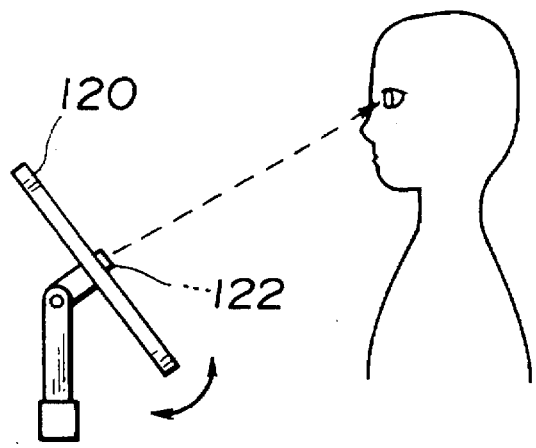

As shown in FIG. 31, a normal display panel 121 of liquid crystal of a flat type is arranged on a display image plane of a display panel 120 according to the embodiment, and a light emitting element 122 of high directivity is arranged as an angle adjusting apparatus on a side surface of the display panel 120. It can be understood that a light outputted from the light emitting element 122 emits a light at a specific angle. Accordingly, as shown in FIG. 32, the light from the light emitting element is confirmed whereby it is possible to adequately adjust or regulate the attack angle of the display 121.

In this manner, the light emitting element which is high in directivity and which serves as angle adjusting apparatus is provided on the display panel which forms the planar surface which is coplanar with or the same as that of the display, whereby it is possible to easily set the attack angle of the display panel to an adequate angle, with the light outputted from the light emitting element serving as a reference.

Figure 33:
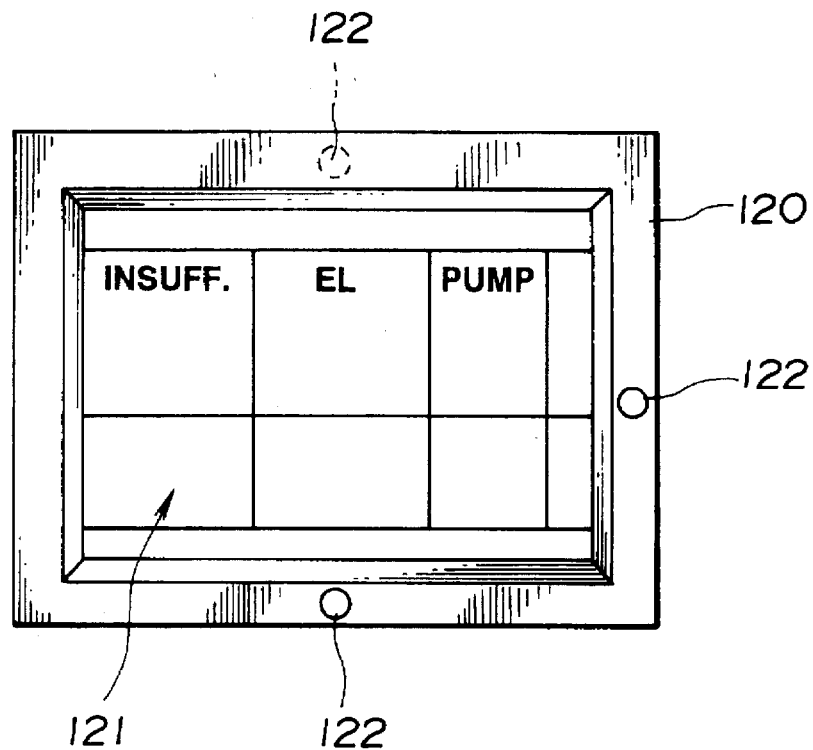
Figure 34:
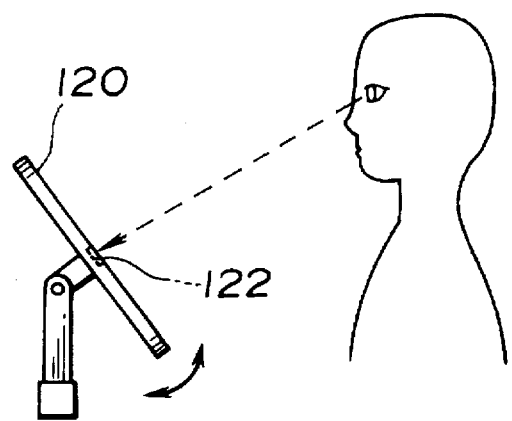

In connection with the above, if the light emitting element that is the angle adjusting apparatus is on the display panel surface which forms the planar surface coplanar with the display, it is possible to freely assign the arrangement position as shown in FIG. 33. Further, the light emitting element is provided so as not to protrude from the display panel surface, as shown in FIG. 34.

Figure 35:
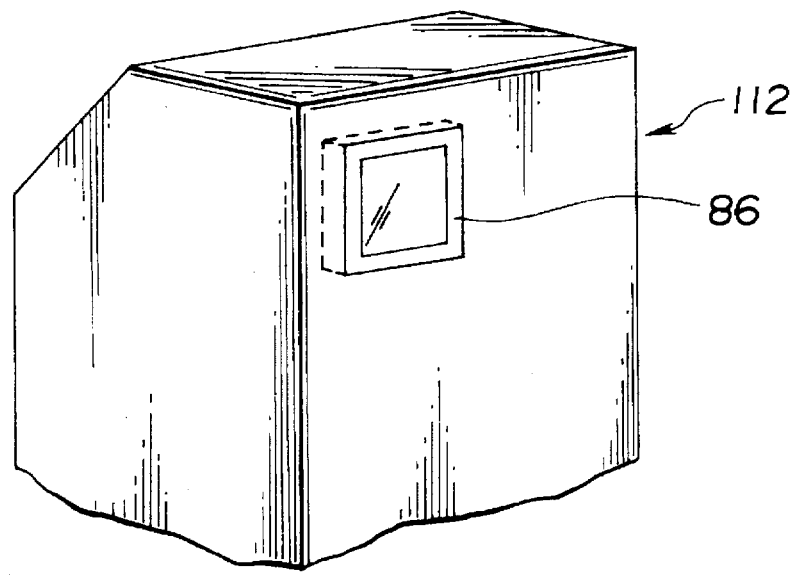

Moreover, as shown in FIG. 35, the display panel 86 of the endoscope operating unit 112 is incorporated into the side surface of the endoscope operating unit 112 on the sterile area, whereby an operator who is positioned within the sterile area can view the contents which are projected on the display panel 86. The operating person in charge does not also stand in the way during operation of the display panel 86.

Figure 36:
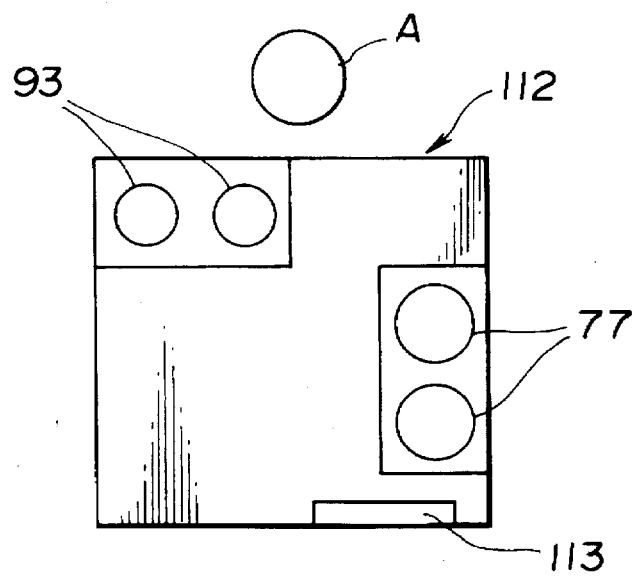

Furthermore, as shown in FIG. 36, the CO2 gas bomb 77 is arranged in the unsterile area on the side surface of the connector group 113; the suction bottle 93 is arranged on the side of the equipment operator on the surface opposite to the connector group 113; and only the connector group 113 is oriented toward the sterile area. Accordingly, since the equipment operator A can perform the operation without the necessity of entering the sterile area, in order to replace the CO2 bomb 77 and to confirm the capacity of the suction bottle 93, the sterile area can be protected from contamination.

Figure 37:
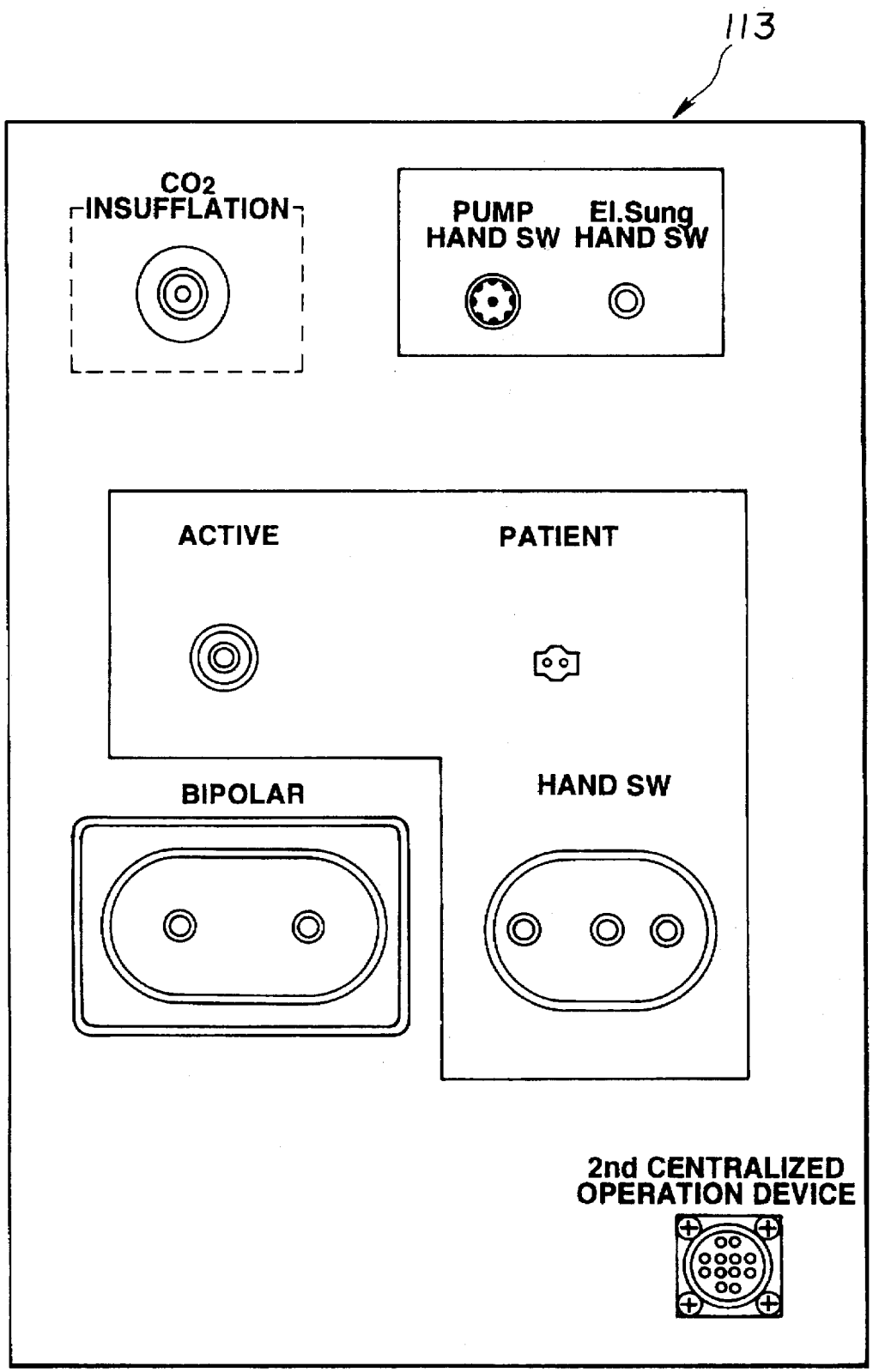

Moreover, as shown in FIG. 37, the plurality of connectors are provided together on the connector group 113, whereby mounting operation of the cables, the tubes or the like, which are used on the operation table 111 in the sterile area is improved. In this connection, the positional relationship between the connector group 113 and the centralized operation device 18 should not be limited to this one. If the connector group is so arranged as to be oriented toward the operation table which is arranged on the side of the sterile area, the centralized operation device may be on the side of the side (lateral) surface.

A sixth embodiment of the invention will be described with reference to FIGS. 38 to 43.

As has been shown in FIG. 25, since the various pieces of medical equipment, the tubes, the cables or the like exist mixed together in the operating chamber, a step or a pace was bad, and the operability was not sufficiently satisfied.

In view of the above, the present embodiment is arranged such that, in place of the communication cables which connect the various pieces of medical equipment and the system controller to each other so as to be capable of performing bidirectional communication, an optical communication device is used whereby the communication cables for the bidirectional communication are eliminated to thereby improve workability or operability within the operating chamber.

Figure 38:
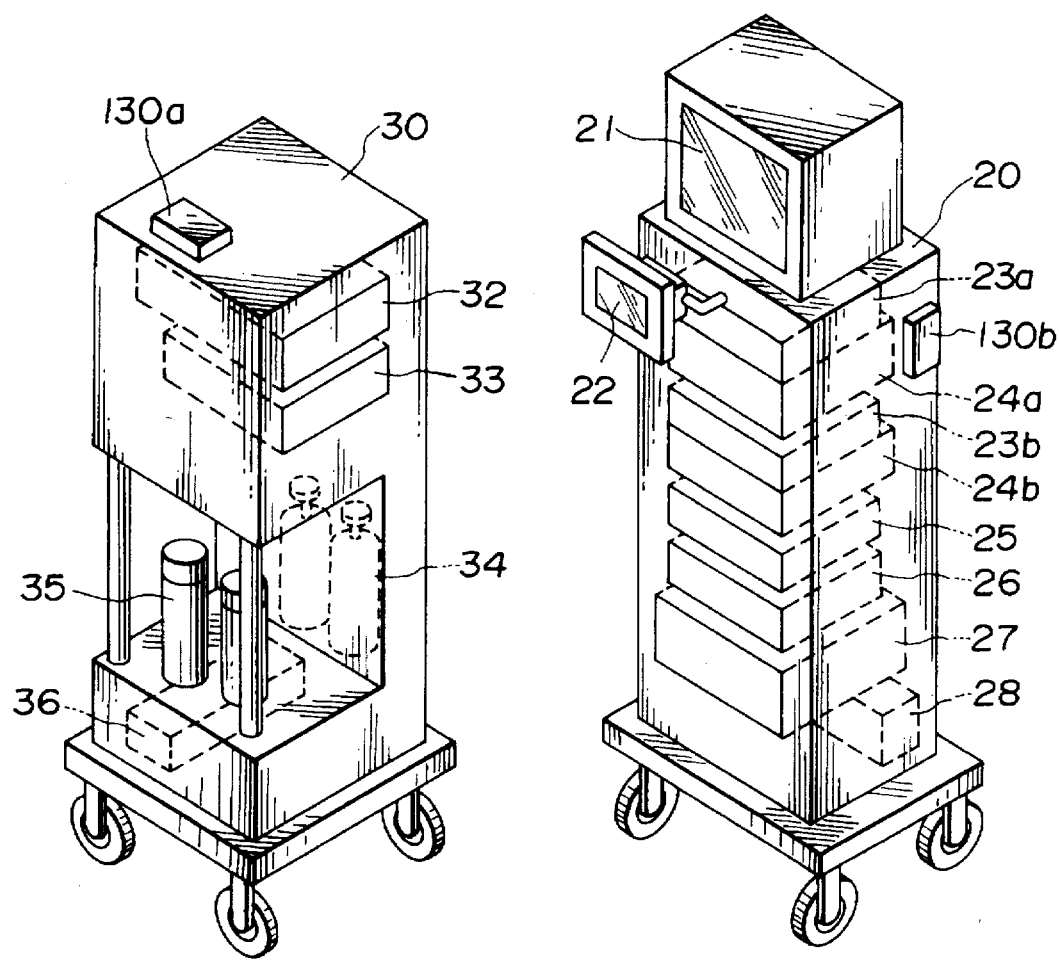

As shown in FIG. 38, in the medical endoscope system, a set of optical communication devices 130a and 130b, for example, is arranged on the first cart 91 and the second cart 92.

Figure 39:
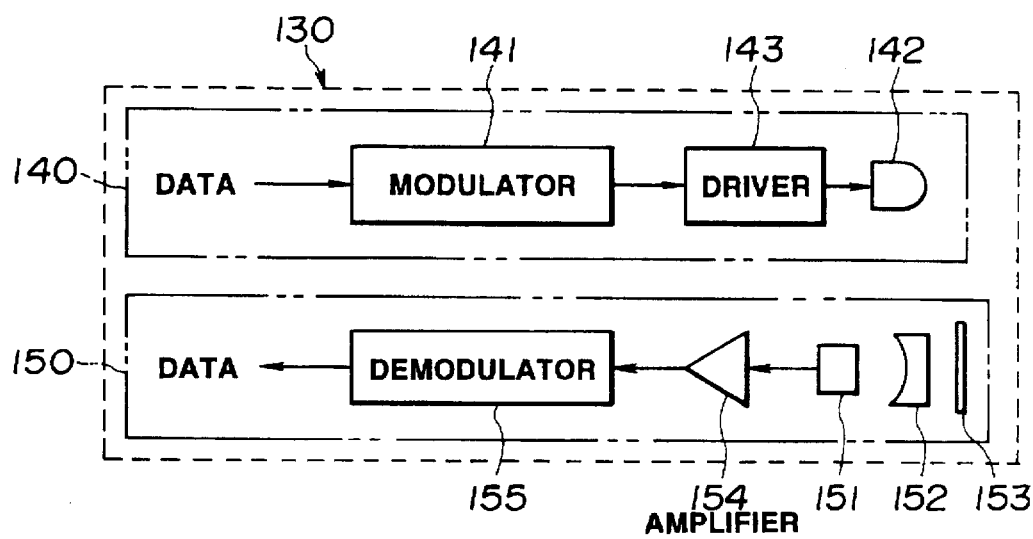

As shown in FIG. 39, an optical communication device 130 is formed by an output side 140 and a light receiving side 150. A modulator 141 for modulating data from the distributors (reference numerals 88 and 94) which are connected to the various pieces of medical equipment, by a modulating system of any one of emphasizing modulation, frequency modulation, phase modulation, amplitude modulation, spectrum diffusion or the like, and a driver 143 for driving a light source 142 such as an LED, an SLD or the like for radiating a signal modulated by the modulator 141, to a space are provided on the output side 140.

Meanwhile, a detector 151 for receiving a diffused light and a direct light which are outputted from the output side 140 of the mating optical communication device 130, a condenser lens 152 arranged on a front surface of the detector 151 for effectively condensing the diffused light and the direct light, a band pass filter 153 for cutting off wavelength (noise) other than the optical communication device such as a light of a fluorescent lamp within a chamber, an amplifier 154 for amplifying a signal which is inputted to the detector 151, and a demodulator 155 for demodulating a signal which is modulated by the modulator 141 on the output side 140 are provided on the light receiving side 150 of the optical communication device 130.

A medical system control apparatus which is provided with the optical communication device 130 arranged as described above will be described.

Figure 40:
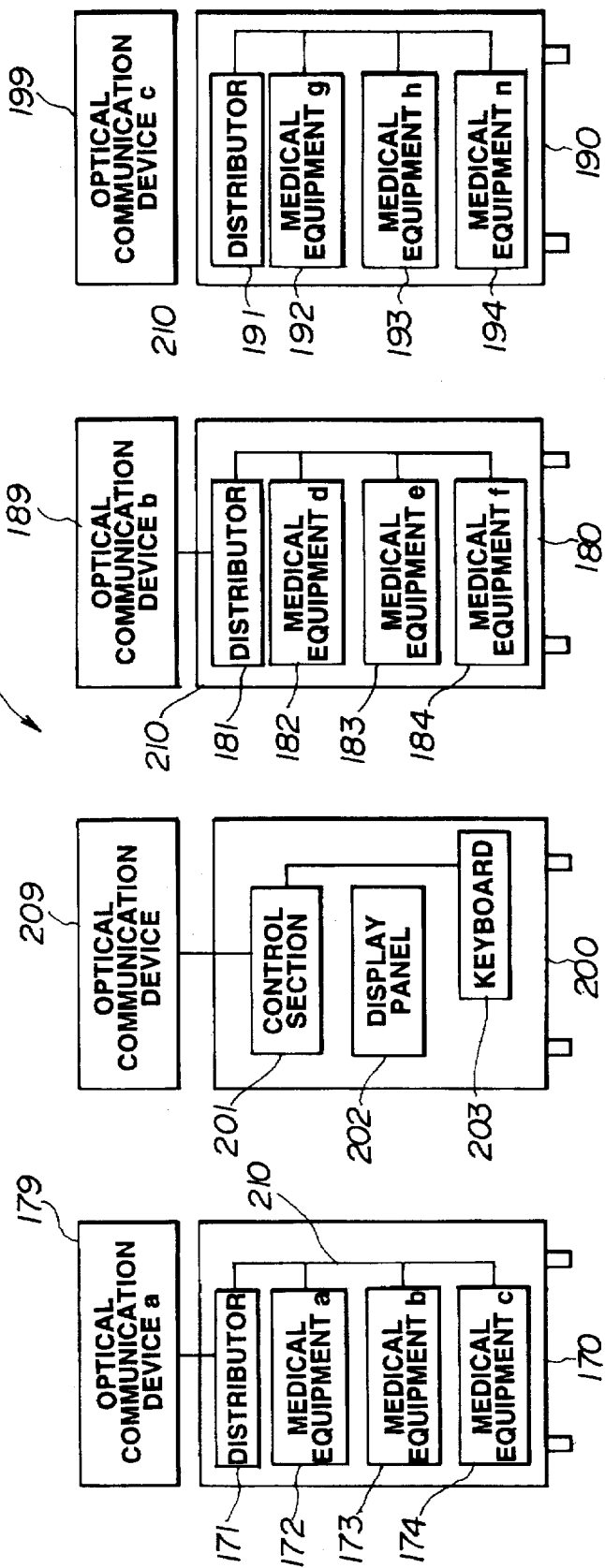

As shown in FIG. 40, the medical system control apparatus 160 comprises a first cart 170, a second cart 180 and a third cart 190 which load the plurality of pieces of medical equipment, and a control cart 200.

For example, the arrangement is as follows. That is, a distributor 171, a piece of medical equipment a 172, a piece of medical equipment b 173, a piece of medical equipment c 174 and an optical communication device a 179 are loaded on a first cart 170. A distributor 181, a piece of medical equipment d 182, a piece of medical equipment e 183, a piece of medical equipment f 184 and an optical communication device b 189 are loaded on a second cart 180. A distributor 191, a piece of medical equipment g 192, a piece of medical equipment h 193, a piece of medical equipment n 194 and an optical communication device c 199 are loaded on a third cart 190. An optical communication device 209 which performs communication to the optical communication devices 179, 189 and 199 which are loaded respectively on the first cart 170, the second cart 180 and the third card 190, a control section 201 for controlling the various pieces of medical equipment, a display panel 202 and a keyboard 203 for centralized control are loaded on a control cart 200.

The plurality of pieces of medical equipment which are loaded on these carts 170, 180 and 190 are arranged such that a plurality of pieces of medical equipment within these carts and the distributors 171, 181 and 191 distribute which control signals are connected to each other by a communication code 210 such as, for example, a general purpose interface bus or the like, and the distributors 171, 181 and 191 are connected respectively to the optical communication devices 179, 189 and 199 so that the plurality of pieces of medical equipment which are loaded on these carts 170, 180 and 190 are remote-controlled by transmission and receiving of a light.

Operation of the medical system control apparatus 160 arranged as described above will be described.

First, the keyboard 203 which is provided on the control cart 200 is operated to perform input of setting or modification of data of a plurality of pieces of medical equipment or a single pieces of medical equipment. A signal of the setting or the modification is transmitted to the optical communication device 209. The signal which is transmitted to the optical communication device 209 is modulated as shown in FIG. 39, and is converted to infrared region so as to be radiated.

Next, a signal of the invisible light which is radiated from the optical communication device 209 is received by the optical communication devices 179, 189 and 199 which are loaded respectively on the carts 170, 180 and 190. The modulated signal is demodulated as shown in FIG. 39 and is converted to a predetermined control signal. The control signal is transmitted to the various pieces of medical equipment through the distributors 171, 181 and 191, to perform the setting or the modification of the corresponding data.

In this manner, transmission of the signal is performed by utilization of the light such as an infrared ray or the like in place of a mode of transmission requiring the use of communication cables, whereby the communication cables can be swept away from the operating chamber so that the step or pace within the operating chamber feels refreshed, no obstacle is given or applied to the operator, and an attempt can be made to improve the environment within the operating chamber and to further improve safety. The plurality of pieces of medical equipment can easily combined with each other so as to be systematized.

Figure 41:
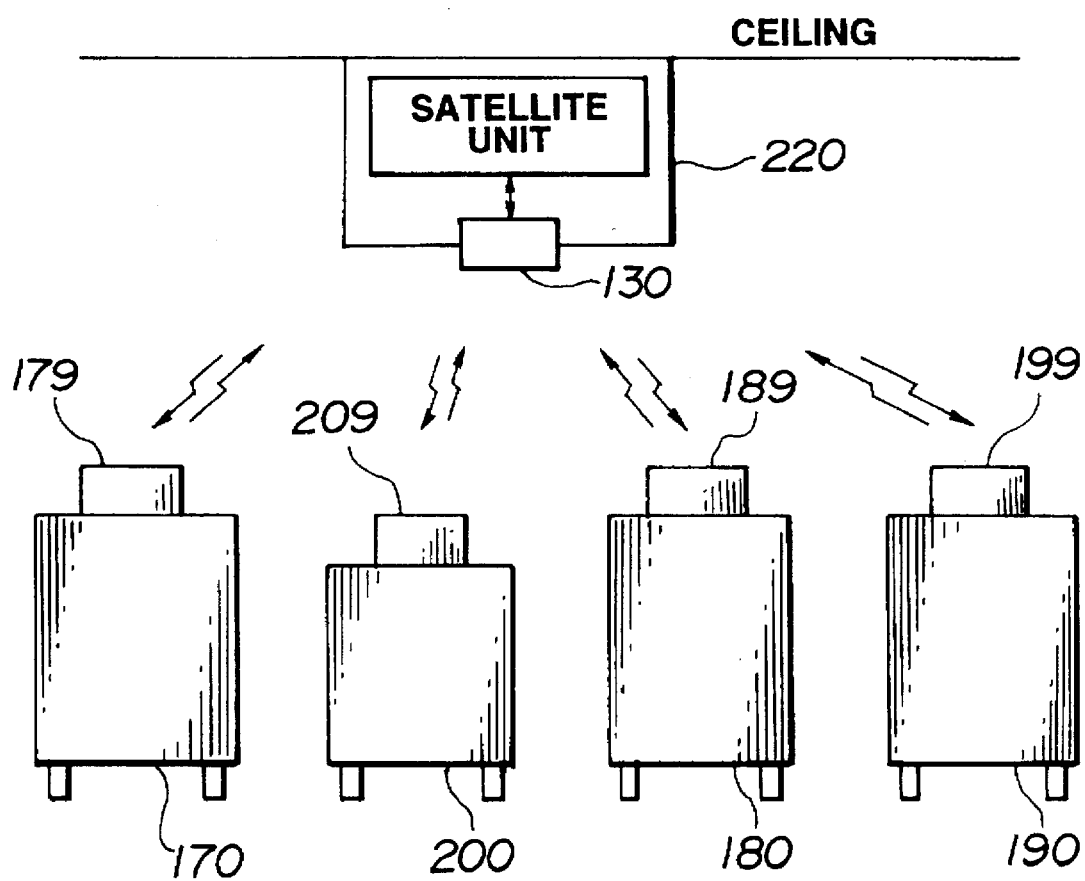

Further, as shown in FIG. 41, a trunk or repeater satellite unit 220 which is provided with the optical communication device 130 is provided at a position where the visibility is good or superior, such as the ceiling of the operating chamber or the like, such that the communication light which is transmitted and received by the optical communication devices 179, 189, 199 and 209 which are provided respectively on the carts 170, 180, 190 and 200 which load thereon the pieces of medical equipment is not interrupted, whereby communication within the broad operating chamber is made possible, and, whenever the optical communication is, by any change, cut off or shut down by an obstacle, the communication through the trunk or repeater satellite unit 220 comes into existence so that control of the various pieces of medical equipment can surely be performed. By the fact that the plurality of trunk or repeater satellite units are arranged within the operating chamber, it is possible to completely eliminate a communication cutoff or shutdown region within the operating chamber.

Moreover, as shown in FIG. 42, in, for example, the medical system control apparatus 230 which comprises the first cart 170, the second cart 180 and the control cart 200, which are not shown, the wavelength of the light which is outputted from the optical communication devices 179, 189 and 209 which are arranged respectively on the carts 170, 180 and 200 is changed.

Specifically, a modulator 175a for outputting a light having wavelength thereof of $\lambda 1$ and a driver 175c which drives a light source 175b such as an LED, an SLD or the like for radiating the signal which is modulated by the modulator 175a, to the space, are provided on the output side 175 of the optical communication device 179 which is arranged on the first cart 170. A band pass filter 176a which cuts off the wavelength (noise) other than the optical communication device such as a light of a fluorescent lamp within the chamber to pass only the wavelength of $\lambda 3$ which is outputted from the light source 205b which is provided on the output side 205 provided on the control cart 200, an amplifier 176c for amplifying the signal which is inputted to the detector 176c, and a demodulator 176d for demodulating the signal which is modulated by the modulator 205a on the output side are provided on the input side 175.

Further, a modulator 185a for outputting a light having wavelength thereof of $\lambda 2$ and a driver 185c which drives a light source 185b such as an LED, an SLD or the like for radiating the signal modulated by the modulator 185a, to the space, are provided on an output side 185 of an optical communication device 189 which is arranged on the second cart 180. Provided on an input side 186 are a band pass filter 186a for cutting off the wavelength (noise) other than the optical communication device to pass therethrough only the wavelength of $\lambda 3$ which is outputted from a light source 205b which is provided on the output side 205 provided on a control cart 200, an amplifier 186c for amplifying the signal which is inputted to the detector 186b and a demodulator 186d for demodulating the signal which is modulated by a modulator 205a on the output side.

Moreover, the modulator 205a for outputting wavelength of $\lambda 3$ and a driver 205c which drives the light source 205b such as an LED, an SLD or the like for radiating the signal modulated by the modulator 205a, to the space, are provided on the output side of the control cart 200. Provided on the input side are a band pass filter 206a for allowing only a light having wavelength of $\lambda 1$ which is outputted from the optical communication device 179 arranged on the first cart 170 as a first input side 206, to pass therethrough, an amplifier 206c for amplifying the signal which is inputted to the detector 206b and a demodulator 206d for demodulating the signal which is modulated by the modulator 175a on a second output side. Provided on a second input side 207 are a band pass filter 207a for allowing only a light having wavelength of $\lambda 2$ which is outputted from the optical communication device 189 arranged on the second cart 180 to pass therethrough, an amplifier 207c for amplifying the signal which is inputted to a detector 207b and a demodulator 207d for demodulating the signal which is modulated by the modulator 185a on the output side.

In this manner, the wavelengths are respectively set by communication directions of the communication devices, whereby it is possible to realize large or high capacity of transmitted information. In this connection, at this time, light receiving portions of the numbers corresponding to the optical communication devices which are arranged on the communicating carts are provided on the optical communication devices which are arranged on the control cart. In place of the optical communication devices, although there is a problem that a noise is generated, it is also possible to perform transmission and receiving of data due to waves.

In connection with the above, although the invention has been described such that the medical system control apparatus is the medical endoscope system, the medical system control apparatus should not be limited to the medical endoscope system. Further, the arrangement positions of the communication connector and the display panel to the carts should not be limited to the positions illustrated in the drawings.

In this invention, it is apparent that working modes or embodiments different in a wide range from each other can be formed on the basis of this invention without departing from the spirit and scope of the invention. This invention should not be restricted by any specific embodiment except being limited by the appended claims.

What is claimed is:

1. A medical system control apparatus comprising:

a plurality of pieces of medical equipment each having an identification number, the plurality of pieces of medical equipment having respective display portions on which one of setting conditions and operating conditions is displayed and respective operating portions for modifying one of the setting conditions and the operating conditions which are displayed on said display portions;

control means for controlling, in a centralized manner, said plurality of pieces of medical equipment;

centralized display means connected to said control means and provided with a display portion which displays the display contents of said plurality of pieces of medical equipment;

centralized operation means connected to said control means for controlling one of the setting conditions and the operating conditions which are displayed on said display portions of said pieces of medical equipment; and communication means for enabling said plurality of pieces of medical equipment, said centralized display means and said centralized operation means and said control means being adapted to communicate with each other in a bidirectional manner where one of the setting conditions and the operating conditions of said pieces of medical equipment is operable by any one of the operating portions and the centralized operation means which are provided respectively on the pieces of medical equipment, wherein operating indications from the operating portions of the pieces of medical equipment have priority over an operating indication from the centralized operation means.

2. A medical system control apparatus according to claim 1, wherein, when one of the setting conditions and the operating conditions of said pieces of medical equipment is operated by one of the operating portions and the centralized operation means which are provided on the piece of medical equipment, operating indications from the operating portions of the pieces of medical equipment have priority over an operating indication from the centralized operation means.

3. A medical system control apparatus according to claim 1, wherein said plurality of pieces of medical equipment are loaded on at least one cart, and wherein a distributor is provided on the cart which loads the pieces of medical equipment.

4. A medical system control apparatus according to claim 3, wherein a cart on which said plurality of pieces of medical equipment are loaded is arranged in an unsterile area, and wherein a proximal end of one of cables and tubes which extend out from said cart toward a sterile area is provided so as to be opposed against the sterile area side.

5. A medical system control apparatus according to claim 4, wherein the operating portion of the medical equipment which is loaded on said cart and which is adaptable to be operated by a person in charge who is in the unsterile area, and an exchange port of the medical equipment which requires exchanging are so arranged as to be isolated from the sterile area.

6. A medical system control apparatus according to claim 1, wherein said communication means is a communication cable.

7. A medical system control apparatus according to claim 1, wherein at least one of said centralized display means and said centralized operation means is arranged within the operating chamber, and wherein, when one of said centralized display means and said centralized operation means which is arranged within said operating chamber moves, one of said centralized display means and the display portion of said centralized operation means is so operated as to be interlocked therewith so as to be opposed against a person in charge.

8. A medical system control apparatus according to claim 7, wherein said centralized display means and the display portion of said centralized operation means is provided with a light emitting element having high directivity as an attack-angle recognition means.

9. A medical system control apparatus according to claim 1, wherein said communication means is an optical communication means, and wherein an optical communication device is provided on at least one set of at least one cart which loads said plurality of pieces of medical equipment, the centralized display means, the centralized operation means and said control means.

10. A medical system control apparatus according to claim 9, wherein said optical communication device comprises an output side which is provided with a modulator, a communication light source and a driver for driving the communication light source, and an input side which is provided with a detector, a condensing lens, a band pass filter, an amplifier and a demodulator.

11. A medical system control apparatus according to claim 9, wherein the optical communication device which is provided on at least one set of said plurality of carts, the centralized display means, said centralized operation means and said control means performs optical communication through a repeating satellite unit.

12. A medical system control apparatus according to claim 9, wherein wavelengths of a light which is used in the optical communication of said optical communication device are set so as to be different from every other communication device.

13. A medical system control apparatus comprising:

a plurality of pieces of medical equipment having respective identification numbers thereof individually, and having respective display portions on which one of setting conditions and operating conditions is displayed and respective operating portions for modifying one of the setting conditions and the operating conditions which are displayed on said display portions;

control means for controlling, in a centralized manner, said plurality of pieces of medical equipment; and communication means for enabling said plurality of pieces of medical equipment and said control means to be communicated, in a bidirectional manner, with each other, wherein at least one of centralized display means provided with a display portion for displaying the display contents of the plurality of pieces of medical equipment and centralized operation means having a display portion for displaying the display contents of the plurality of pieces of medical equipment, said centralized operation means which control one of the setting conditions and the operating condition of the pieces of medical equipment is connected to said control means, and wherein at least one of said centralized display means and the display portion of said centralized operation means has an image plane which displays the contents of a specific function of the plurality of pieces of medical equipment.

14. A medical system control apparatus according to claim 13, wherein at least one of said centralized display means and the display portion of said centralized operation means has an image plane which displays the operating portion which performs modification of one of the setting conditions and the operating conditions which are had respectively by the plurality of pieces of medical equipment.

15. A medical system control apparatus according to claim 13, wherein the display image plane of the display portion of said centralized operation means has a backup image plane for storing a predetermined operating condition of the pieces of medical equipment which is extracted from the plurality of pieces of medical equipment.

16. A medical system control apparatus according to claim 13, further including a plurality of centralized display means and a plurality of centralized operation means, wherein at least one of the plurality of centralized display means and the plurality of said centralized operation means is connected to said control means, and wherein the display contents which are displayed on one of said centralized display means and the display portion of said centralized operation means are set from every one of said centralized display means and said centralized operation means.

17. A medical system control apparatus according to claim 16, wherein the control contents of the plurality of centralized operating means which are connected to said control means are set from the plurality of pieces of medical equipment, and wherein the pieces of medical equipment are operated respectively by the centralized operation means.

18. A medical system control apparatus according to claim 17, wherein said centralized operation means of at least one of the plurality of centralized operation means which are connected to the control means controls all the pieces of medical equipment which form a system.

19. A medical system control apparatus according to claim 17, wherein said centralized operation means of at least one of the plurality of centralized operation means which are connected to the control means is arranged within a sterile operation chamber.

20. A medical system control apparatus according to claim 17, wherein, when a plurality of control signals are inputted to the control means from said plurality of centralized operation means within a predetermined period of time, the control means assigns different levels of priority to each of the plurality of control signals and the control signal from said operating means which is highest in priority level is processed first.

21. A medical system control apparatus according to claim 20, wherein, when said plurality of centralized operation means are provided on a sterile area and an unsterile area of an operating chamber, the centralized operation means which is arranged within the sterile area has a higher priority than the centralized operation means which is arranged in the unsterile area.

22. An image-plane display method of medical system control apparatus, comprising:

controlling, in a centralized manner, a plurality of pieces of medical equipment having respective identification numbers thereof individually and having respective display portions on which one of setting conditions and operating conditions is displayed, and respective operating portions for modifying one of the setting conditions and the operating conditions which is displayed on said display portion, through control means;

displaying the display contents of said plurality of pieces of medical equipment which are controlled by said control method, onto a centralized display means;

displaying the display contents of the plurality of pieces of medical equipment which are controlled by said control method onto a centralized operation means, for controlling one of the setting conditions and the operating conditions which are displayed on said display portions of the pieces of medical equipment; and bidirectionally communicating between the centralized display means, said centralized operation means and the control means, wherein an image plane which displays the contents of specific functions of said plurality of pieces of medical equipment, an image plane which displays the contents of one of the setting conditions and the operating conditions which are displayed on said display portions which are displayed respectively on said plurality of pieces of medical equipment, and a backup image plane for storing a predetermined operating condition of the pieces of medical equipment which is extracted from said plurality of pieces of medical equipment are hierarchically displayed on at least one of centralized display means which is provided with a display portion for displaying one of the setting conditions and the operating conditions of the plurality of pieces of medical equipment and a display portion of centralized operation means for controlling one of the setting conditions and the operating conditions of the pieces of medical equipment.

23. An image-plane display method of medical system control apparatus according to claim 22, further comprising the step of selecting image planes of said hierarchy image planes respectively by selective switches which are provided on parts of the respective image planes.

24. An image-plane display method of medical system control apparatus according to claim 22, further comprising the step of setting priority levels beforehand respectively to the plurality of pieces of medical equipment which are connected to said control means, wherein said hierarchy image planes are so arranged as to be in order from highest to lowest in accordance with the priority levels of pieces of said medical equipment.

25. An image-plane display method of medical system control apparatus according to claim 22, further comprising the step of informing abnormality of a system onto the hierarchy image plane which is displayed on at least one of said centralized display means and the display portion of said centralized operation means.

26. An image-plane display method of medical system control apparatus according to claim 25, wherein, in said informing step, when the abnormality is detected, abnormality information is displayed on the image plane, and a tone of color of a display region of the medical equipment corresponding to the abnormality information is changed.

27. An image-plane display method of medical system control apparatus according to claim 25, wherein, in said informing step, when the abnormality is detected, abnormality information is displayed on the image plane, and a display region of the medical equipment corresponding to the abnormality information is turned on and off.

28. An image-plane display method of medical system control apparatus according to claim 25, wherein, in said informing step, the display regions of the medical equipment in which the abnormality is detected are erased from the hierarchy image plane.

* * * * *